United States Patent [19]
Yamaguchi et al.

[11] Patent Number: 4,578,395
[45] Date of Patent: Mar. 25, 1986

[54] CERTAIN ARALKYLAMINOALKYL ESTERS OF 1,4 DIHYDROPYRIDINES AS ANTIHYPERTENSIVE

[75] Inventors: Hisao Yamaguchi; Hideo Kanno; Yoshiaki Okamiya, all of Hino; Kiyotaka Sunakawa, Tokyo, all of Japan

[73] Assignee: Teijin Limited, Osaka, Japan

[21] Appl. No.: 616,515

[22] Filed: Jun. 1, 1984

[30] Foreign Application Priority Data

Jun. 2, 1983 [JP] Japan .................................. 58-96995
Jun. 8, 1983 [JP] Japan .................................. 58-100857
Nov. 9, 1983 [JP] Japan .................................. 58-209178

[51] Int. Cl.⁴ .................. C07D 211/90; A61K 31/455
[52] U.S. Cl. ..................................... 514/356; 546/321
[58] Field of Search ................ 546/321; 424/266; 514/356

[56] References Cited

U.S. PATENT DOCUMENTS 3,985,758 10/1976 Murakami et al. ................... 546/321
4,264,611 4/1981 Berntsson et al. ................... 546/321

FOREIGN PATENT DOCUMENTS 0101365 8/1975 Japan .................................. 546/321
0031663 2/1982 Japan .................................. 546/321
1383625 2/1975 United Kingdom ............... 546/321

*Primary Examiner*—Henry R. Jiles
*Assistant Examiner*—Dale A. Bjorkman
*Attorney, Agent, or Firm*—Sughrue, Mion, Zinn, Macpeak, and Seas

[57] ABSTRACT

A 1,4-dihydropyridine derivative of the formula

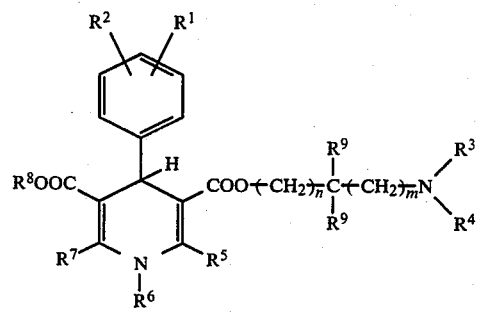

wherein $R^1$ and $R^2$ are identical or different and each represents a hydrogen atom, a halogen atom or a nitro group, provided that $R^1$ and $R^2$ are not hydrogen atoms at the same time; $R^3$ represents an alkyl group; $R^4$ represents an aralkyl group which may be substituted; $R^5$ and $R^7$ are indentical or different and each represents an alkyl group; $R^6$ represents a hydrogen atom or an alkyl group; $R^8$ represents an alkyl group; $R^9$ represents a hydrogen atom or an alkyl group; n and m are identical or different and each represents an integer of 0 to 6; provided that when either one of $R^1$ and $R^2$ is a hydrogen atom, $R^9$ is an alkyl group;

or an acid addition salt thereof.

The 1,4-dihydropyridine derivative is characterized by a strong antihypertensive activity and the long duration of the activity.

11 Claims, No Drawings

CERTAIN ARALKYLAMINOALKYL ESTERS OF 1,4 DIHYDROPYRIDINES AS ANTIHYPERTENSIVE

BACKGROUND OF THE INVENTION

1. Field of the Invention

The present invention relates to a 1,4-dihydropyridine derivative, a process for the production thereof, and the pharmaceutical use thereof. More particularly, this invention relates to a novel 1,4-dihydropyridine derivative which is characterized by a strong pharmacological action such as antihypertensive action, vasodilative action, etc. and the long duration of pharmacological action, a process for the production thereof, and the pharmaceutical use thereof.

2. Description of the Prior Art

Various 1,4-dihydropyridine derivatives have hitherto been made known as compounds having such pharmacological action as antihypertensive action, vasodilative action, etc. For instance, 4-(2-nitrophenyl)-2,6-dimethyl-1,4-dihydropyridine-3,5-dicarboxylic acid dimethyl ester (hereinafter referred to as Nifedipine) is known to have a strong pharmacological action such as coronary vasodilative action, etc. (U.S. Pat. No. 3,644,627) and is now generally used as a remedy for angina pectoris. Though Nifedipine is a compound which has an excellent pharmacological activity, it has some demerits of being purely soluble in water, chemically very unstable, and short in durability of its pharmacological activity.

A wide variety of Nifedipine derivatives have hitherto been proposed. For example, 4-(2,3-dichlorophenyl)-2,6-dimethyl-1,4-dihydropyridine-3,5-dicarboxylic acid-3-methyl ester-5-ethyl ester (hereinafter referred to as Felodipine) represented by the undermentioned formula is known (Japanese Patent Application Laid-Open No. 9083/'80).

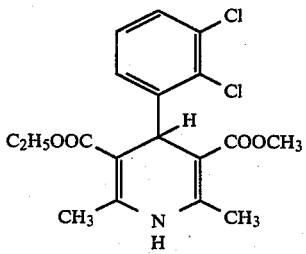

Felodipine is a 1,4-dihydropyridine derivative which has a 2,3-disubstituted phenyl group at the 4-position and has an action to selectively dilate the peripheral vascular tracts (Japanese Patent Application Laid-Open No. 9083/'80, Official Gazette p. 2, left lower section, lines 13-16). However, this compound is very purely soluble in water and its vasodilative action is not strong enough.

Another example of 1,4-dihydropyridine derivative represented by the following formula is described in Japanese Patent Application Laid-Open No. 24277/'75

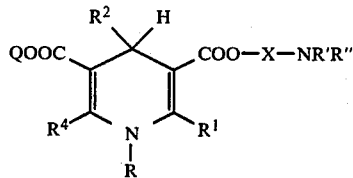

wherein R is a hydrogen atom, or a linear or branched saturated aliphatic group; R' and R" are identical or different and each represents a hydrogen atom or an alkyl group; $R^2$ is an aryl group (which may have 1, 2 or 3 substituents groups discretionally selected from among nitro, cyano, azido, alkyl, alkoxy, acyloxy, alkoxycarbonyl, amino, acylamino, alkylamino, dialkylamino, SOn-alkyl (wherein n=0, 1 or 2), phenyl, trifluoromethyl and halogen atoms); Q is a straight-chain, brached-chain, or cyclic saturated or unsaturated hydrocarbon chain which may discretionally contain one or two hydroxyl groups as substituents and may be interrupted discretionally by one or two oxygen atoms; $R^1$ and $R^4$ are identical or different and each represents a hydrogen atom or a linear or branched alkyl group; and X represents a linear or branched alkylene group.

This compound has a N,N-dialkylaminoalkoxycarbonyl group (—COO—X—NR'R") as the substituent as the 5-position. It is disclosed that this compound is capable of dilating the coronary blood vessel remarkably extending over a long period of time (Japanese Patent Application Laid-Open No. 24277/'75, Official Gazette p. 17, left lower section, lines 3-9). However, this 1,4-dihydropyridine derivative is not satisfactory enough in both antihypertensive action and duration of action, according to the study made by the inventors of the present invention.

Also, U.S. Pat. No. 3,985,758 describes, for example, 1,4-dihydropyridine derivative expressed by the following formula

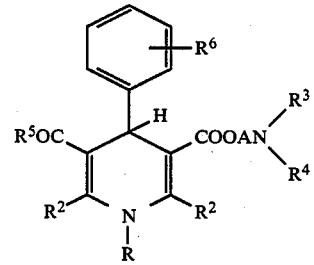

wherein R represents hydrogen or lower alkyl; $R^1$ and $R^2$ represent methyl respectively; $R^3$ represents phenyl, benzyl, halobenzyl, or alkoxybenzyl; $R^4$ represents hydrogen, methyl or ethyl; A represents lower alkylene; $R^5$ represents methyl, or lower alkoxy, or lower alkoxy with lower alkoxy; and $R^6$ represents nitro or trifluoromethyl.

As the most typical of such compounds, 4-(3-nitrophenyl)-2,6-dimethyl-1,4-dihydropyridine-3,5-dicarboxylic acid-3-methyl ester-5-β-(N-benzyl-N-methylamino) ethyl hydrochloride (hereinafter referred to as Nicardipine) is especially known widely. This type of compound is structurally characterized in that it has a monosubstituted phenyl group at the 4-position and an N-alkyl-N-aralkylaminoalkoxycarbonyl group at the 5-position. U.S. Pat. No. 3,985,758 also discloses that these compounds have cerebral vascular dilator activity and high water-solubility.

However, U.S. Pat. No. 3,985,758 neither gives description as to the concrete examples of the 1,4-dihydropyridine derivative which has an N-alkyl-N-aralkylamino branched alkoxycarbonyl group at the 5-position nor makes reference to the 1,4-dihydropyridine derivative which has a disubstituted phenyl group at the 4-position. U.S. Pat. No. 3,985,758 also remains utterly silent about the duration of pharmacological actions of 1,4-dihydropyridine derivatives.

The studies made by the inventors of the present invention has revealed that the 1,4-dihydropyridine derivatives represented by Nicardipine, etc. have not strong enough pharmacological activities including an antihypertensive action, etc. and that the duration of action is not long enough either.

SUMMARY OF THE INVENTION

A primary object of this invention is to provide a novel 1,4-dihydropyridine derivative having a highly potential pharmacological action such as antihypertensive action, vasodilative action, etc.

A further and separate object of this invention is to provide a novel 1,4-dihydropyridine derivative having a highly potential pharmacological action such as antihypertensive action, vasodilative action, etc. and also the long duration of pharmacological action.

A further and separate object of this invention is to provide a novel 1,4-dihydropyridine derivative which is a compound having a disubstituted phenyl group at the 4-position and an N-alkyl-N-aralkyl amino straight or branched alkoxycarbonyl group at the 5-position and has not yet been disclosed concretely in the prior art.

A further and separate object of this invention is to provide a novel 1,4-dihydropyridine derivative which is a compound having a monosubstituted phenyl group at the 4-position and an N-alkyl-N-aralkyl amino branched alkoxycarbonyl group at the 5-position and has not yet been disclosed concretely in the prior art.

A further and separate object of this invention is to provide a novel 1,4-dihydropyridine derivative which has a high $Ca^{++}$ entry blocking action and specific pharmacological action.

A further and separate object of this invention is to provide a novel 1,4-dihydropyridine which is chemically stable enough.

A further and separate object of this invention is to provide a process for preparing a novel 1,4-dihydropyridine derivative.

A further and separate object of this invention is to provide a novel 1,4-dihydropyridine derivative which is a kind of 1,4-dihydropyridine derivative having much less asymmetric carbon atoms contained in its molecules and accordingly can be used as medical and pharmaceutical products with ease.

A further and separate object of this invention is to provide a medicament or a method of medication for curing circulatory system diseases wherein a novel 1,4-dihydropyridine derivative is used.

Other objects and advantages of this invention will become apparent from the following description.

In accordance with this invention, these objects and advantages are achieved by a 1,4-dihydropyridine derivatives of the following formula (1)

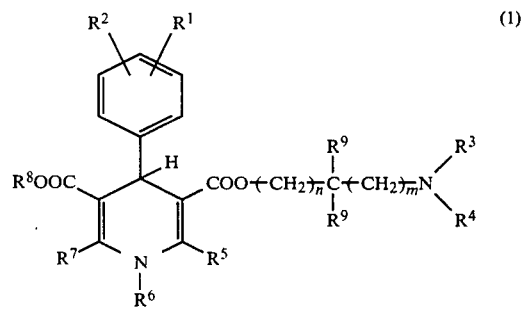

wherein
$R^1$ and $R^2$ are identical or differend and each represents a hydrogen atom, a halogen atom or a nitro group, provided that $R^1$ and $R^2$ are not hydrogen atoms at the same time; $R^3$ represents an alkyl group;
$R^4$ represents an aralkyl group which may be substituted; $R^5$ and $R^7$ are identical or different and each represents an alkyl group;
$R^6$ represents a hydrogen atom or an alkyl group; $R^8$ represents an alkyl group; $R^9$ represents a hydrogen atom or an alkyl group; n and m are identical or different and each represents an integer of 0 to 6; provided that when either one of $R^1$ and $R^2$ is a hydrogen atom, $R^9$ is an akyl group;
or an acid addition salt thereof.

DESCRIPTION OF THE PREFERRED EMBODIMENTS

The 1,4-dihydropyridine derivative expressed by the aforementioned formula (I) can be classified into the undermentioned two types of molecules according to the definitions of the substituents $R^1$, $R^2$ and $R^9$.

(a) 1,4-dihydropyridine derivative in which $R^1$ and $R^2$ in the aforementioned formula (I) are identical or different, each representing a halogen atom or a nitro group and $R^9$ is a hydrogen atom or an alkyl group:

In this case, the 1,4-dehydropyridine derivative of this invention is expressed by the following formula (I)-a.

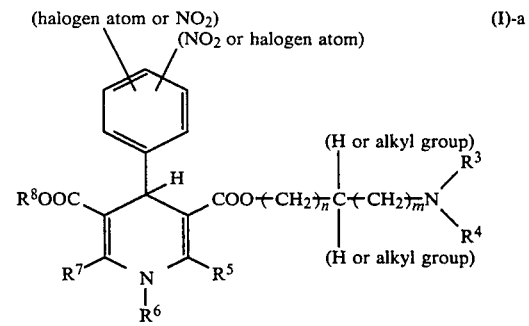

wherein $R^3$, $R^4$, $R^5$, $R^6$, $R^7$, $R^8$, n and m are as defined above.

The 1,4-dihydropyridine derivative of the abovementioned formula (I)-a possesses a structural characteristic of having a disubstituted phenyl group at the 4-position and an N-alkyl-N-aralkylamino straight or branched alkkoxycarbonyl group at the 5-position. The 1,4-dihydropyridine derivative of this invention which possesses such substituents has a highly potential pharmacological action inclusive of antihypertensive action, vasodilative action, etc. and also the remarkably long duration of such pharmacological action. In the 1,4-dihydropyridine derivative, the substituents ($R^1$, $R^2$) of the phenyl group at the 4-position are especially desirable to be present at the 2- and 3-positions or at the 2- and 5-positions since this case allows the 1,4-dihydropyridine derivative to have a highly potential pharmacological action and its long duration. Here, $R^1$ and $R^2$ are nitro groups or halogen atoms, and as the halogen atoms, fluorine, chlorine, bromine, and iodine, for instance, may be mentioned, of which, fluorine and chlorine are particularly desirable.

In the 1,4-dihydropyridine derivative, the substituent ($R^9$) in the ester residue at the 5-position is a hydrogen atom or an alkyl group, and especially $R^9$ should desirably be an alkyl group. In case where $R^9$ is an alkyl group, the 1,4-dihydropyridine derivative of this invention comes to have a remarkably long duration of its pharmacological action. The carbon atom to which $R^9$ is linked has the two identical $R^9$ groups and therefore is not an asymmetric center. This fact makes the 1,4-hydropyridine derivative of this invention have the reduced number of asymmetric carbon atoms in the whole molecules and this hardly requires the resolution of the optical isomers, thus making this derivative desirably suitable for pharmaceutical use. As the alkyl group of $R^9$, $C_1$–$C_6$ alkyl groups such as methyl, ethyl, n-propyl, n-butyl, n-pentyl, n-hexyl, etc., for instance, are desirable, and of them, a methyl group is particularly desirable.

(b) 1,4-dihydropyridine derivative in which either of $R^1$ and $R^2$ in the aforementioned formula (I) is a hydrogen atom and $R^9$ is an alkyl group:

In this case, the 1,4-dihydropyridine derivative of this invention is expressed by the following formula (I)-b.

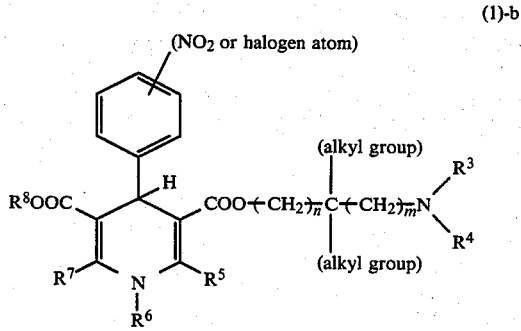

(I)-b wherein $R^3$, $R^4$, $R^5$, $R^6$, $R^7$, $R^8$, n and m are as defined above.

The 1,4-dihydropyridine derivative of the abovementioned formula (I)-b possesses a structural characteristic of having an N-alkyl-N-aralkylamino branched alkoxycarbonyl group at 5-position. The 1,4-dihydropyridine derivative of this invention which possesses such substituents has a highly potential pharmacological action inclusive of antihypertensive actions, etc. and also the remarkably long duration of the pharmacological action. In the 1,4-dihydropyridine derivative of the aforementioned formula (I)-b, the substituent ($NO_2$ or a halogen atom) of the phenyl group at the 4-position should be desirable to be present at the 2- or 3-position. The examples of desirable halogen atom are the same as those given in the case of the 1,4-dihydropyridine derivative of the aforementioned formula (I)-a. As the alkyl group of $R^9$, the same examples as ones mentioned in the 1,4-dihydropyridine derivative of the aforementioned formula (I)-a may again be mentioned. The 1,4-dihydropyridine derivative of this invention in which $R^9$ is an alkyl group is one in which the number of asymmetric carbon atoms contained in its molecules is decreased.

In the foregoing formulae ((1), (1)-a, and (1)-b), $R^3$ represents an alkyl group. Examples of the alkyl group include such linear or branched alkyl groups of 1 to 6 carbon atoms as methyl, ethyl, n-propyl, iso-propyl, n-butyl, sec-butyl, tert-butyl, n-pentyl and n-hexyl. $R^3$ is preferably such a linear alkyl group of 1 to 4 carbon atoms as methyl, ethyl and n-propyl, and more preferably methyl, or ethyl.

$R^4$ represents an aralkyl group which may be substituted. Examples of the aralkyl group are benzyl and phenethyl groups. Examples of the suitable substituents for the substituted aralkyl group are such a halogen atom as fluorine, chlorine and bromine atom; such a $C_1$–$C_6$ alkyl group as methyl, ethyl, n-propyl, n-pentyl and n-hexyl; such a $C_1$–$C_6$ alkoxy group as methoxy, ethoxy, n-propoxy, n-butoxy and n-pentoxy; and such a halogenated methyl group as chloromethyl, dichloromethyl and trifluoromethyl. $R^4$ is preferably a benzyl group which may be substituted. $R^5$ and $R^7$ are identical or different and each represents an alkyl group. Examples of the alkyl group include such a linear or branched $C_1$–$C_6$ alkyl group as methyl, ethyl, n-propyl, iso-propyl, n-butyl, sec-butyl tert-butyl, n-pentyl and n-hexyl. $R^5$ and $R^7$ should preferably be a methyl.

$R^6$ represents a hydrogen atom or an alkyl group. Examples of the alkyl group include such a linear or branched $C_1$–$C_6$ alkyl group as methyl, ethyl, n-propyl, iso-propyl, n-butyl, sec-butyl, tert-butyl, n-pentyl and n-hexyl. $R^6$ should preferably be a hydrogen atom.

$R^8$ represents an alkyl group. Examples of the alkyl group include such a linear or branched $C_1$–$C_{10}$ alkyl group as methyl, ethyl, n-propyl, iso-propyl, n-butyl, sec-butyl, tert-butyl, n-pentyl, n-hexyl, n-heptyl, n-octyl, n-nonyl and n-decyl.

In the aforementioned formulae ((1), (1)-a, and (1)-b), n and m are identical or different and each represents an integer of zero to 6, and preferably an integer of 1 to 3.

The 1,4-dihydropyridine derivative of this invention expressed by the aforementioned formulae may be acid addition salts. The acid addition salts may be salts with inorganic acids, organic carboxylic acid or organic sulfonic acids, preferably inorganic acids, especially preferably mineral acids.

Examples of the acid include such mineral acids as hydrochloric acid, hydrobromic acid, sulfuric acid and phosphoric acid; such organic carboxylic acid as acetic acid, propionic acid, oxalic acid, citric acid, mandelic acid, maleic acid, fumaric acid, lactic acid and glutamic acid; and such organic sulfonic acid as methanesulfonic acid, ethanesulfonic acid, benzenesulfonic acid, p-toluenesulfonic acid and cumylsulfonic acid.

Specific examples of the compounds of formula (1) provided by this invention are shown below.

Compounds of formula [1]-a (100) 2-(N-Benzyl-N-methylamino)ethyl methyl 2,6-dimethyl-4-(2,3-dichlorophenyl)-1,4-dihydropyridine-3,5-dicarboxylate
(102) 2-(N-Benzyl-N-methylamino)ethyl methyl 2,6-dimethyl-4-(2-chloro-3-nitrophenyl)-1,4-dihydropyridine-3,5-dicarboxylate (104) 2-(N-Benzyl-N-methylamino)ethyl methyl 2,6-dimethyl-4-(2-fluoro-3-nitrophenyl)-1,4-dihydropyridine-3,5-dicarboxylate
(106) 2-(N-Benzyl-N-methylamino)ethyl methyl 2,6-dimethyl-4-(3-chloro-2-fluorophenyl)-1,4-dihydropyridine-3,5-dicarboxylate
(108) 2-(N-Benzyl-N-methylamino)ethyl methyl 2,6-dimethyl-4-(3-chloro-2-nitrophenyl)-1,4-dihydropyridine-3,5-dicarboxylate
(110) 2-(N-Benzyl-N-methylamino)ethyl methyl 2,6-dimethyl-4-(2-chloro-3-fluorophenyl)-1,4-dihydropyridine-3,5-dicarboxylate
(112) 2-(N-Benzyl-N-ethylamino)ethyl methyl 2,6-dimethyl-4-(2,3-dichlorophenyl)-1,4-dihydropyridine-3,5-dicarboxylate
(114) 2-(N-4-Fluorobenzyl-N-ethylamino)ethyl methyl 2,6-dimethyl-4-(2-chloro-3-nitrophenyl)-1,4-dihydropyridine-3,5-dicarboxylate
(116) 3-(N-Benzyl-N-ethylamino)propyl methyl 2,6-dimethyl-4-(3-chloro-2-fluorophenyl)-1,4-dihydropyridine-3,5-dicarboxylate
(118) 2-(N-Benzyl-N-propylamino)ethyl methyl 2,6-dimethyl-4-(2-fluoro-5-nitrophenyl)-1,4-dihydropyridine-3,5-dicarboxylate
(120) 2-(N-Benzyl-N-methylamino)ethyl methyl 2,6-dimethyl-4-(2-fluoro-5-chlorophenyl)-1,4-dihydropyridine-3,5-dicarboxylate
(122) 2-(N-4-Methoxybenzyl-N-propylamino)ethyl ethyl 2,6-dimethyl-4-(2-chloro-5-nitrophenyl)-1,4-dihydropyridine-3,5-dicarboxylate
(124) 2-(N-Phenetyl-N-methylamino)ethyl propyl 2,6-dimethyl-4-(2-chloro-5-nitrophenyl)-1,4-dihydropyridine-3,5-dicarboxylate
(126) 3-(N-4-Trifluoromethylbenzyl-N-methylamino) propyl methyl 2,6-dimethyl-4-(2-chloro-5-nitrophenyl)-1,4-dihydropyridine-3,5-dicarboxylate
(128) 2-(N-4-Chlorobenzyl-N-methylamino)ethyl methyl 2,6-dimethyl-4-(2-chloro-5-nitrophenyl)-1,4-dihydropyridine-3,5-dicarboxylate
(130) 3-(N-Benzyl-N-methylamino)-2,2-dimethylpropyl methyl 2,6-dimethyl-4-(2-fluoro-3-nitrophenyl)-1,4-dihydropyridine-3,5-dicarboxylate
(132) 3-(N-Benzyl-N-methylamino)-2,2-dimethylpropyl methyl 2,6-dimethyl-4-(3-chloro-2-nitrophenyl)-1,4-dihydropyridine-3,5-dicarboxylate
(134) 3-(N-Benzyl-N-methylamino)-2,2-dimethylpropyl methyl 2,6-dimethyl-4-(2,3-dichlorophenyl)-1,4-dihydropyridine-3,5-dicarboxylate
(136) 3-(N-Benzyl-N-methylamino)-2,2-dimethylpropyl methyl 2,6-dimethyl-4-(2-chloro-3-nitrophenyl)-1,4-dihydropyridine-3,5-dicarboxylate
(138) 3-(N-4-Trifluoromethylbenzyl-N-methylamino)-2,2-diethylpropyl methyl 2,6-dimethyl-4-(2-fluoro-3-nitrophenyl)-1,4-dihydropyridine-3,5-dicarboxylate
(140) 3-(N-Benzyl-N-methylamino)-2,2-dimethylpropyl methyl 2,6-dimethyl-4-(2-fluoro-5-nitrophenyl)-1,4-dihydropyridine-3,5-dicarboxylate
(142) 3-(N-Benzyl-N-methylamino)-2,2-dimethylpropyl methyl 2,6-dimethyl-4-(5-chloro-2-fluorophenyl)-1,4-dihydropyridine-3,5-dicarboxylate
(144) 2-(N-Benzyl-N-methylamino)ethyl methyl 2,6-dimethyl-4-(2-fluoro-5-nitrophenyl)-1,4-dihydropyridine-3,5-dicarboxylate
(146) 3-(N-Benzyl-N-methylamino)-2,2-dimethylpropyl methyl 2,6-dimethyl-4-(2-chloro-5-nitrophenyl)-1,4-dihydropyridine-3,5-dicarboxylate
(148) 3-(N-Benzyl-N-methylamino)-2,2-dimethylpropyl methyl 2,6-dimethyl-4-(2-chloro-5-nitrophenyl)-1,4-dihydropyridine-3,5-dicarboxylate
(150) 3-(N-Benzyl-N-methylamino)-2,2-dimethylpropyl methyl 1,2,6-trimethyl-4-(2-fluoro-5-nitrophenyl)-1,4-dihydropyridine-3,5-dicarboxylate
(152) 4-(N-Benzyl-N-methylamino)-2,2-dimethylbutyl methyl 2,6-dimethyl-4-(2-chloro-5-nitrophenyl)-1,4-dihydropyridine-3,5-dicarboxylate
(154) 2-(N-Benzyl-N-methylamino)ethyl methyl 2,6-dimethyl-4-(2-chloro-5-nitrophenyl)-1,4-dihydropyridine-3,5-dicarboxylate
(156) 3-(N-Benzyl-N-methylamino)-2,2-dimethylpropyl methyl 2,6-dimethyl-4-(3-chloro-2-fluorophenyl)-1,4-dihydropyridine-3,5-dicarboxylate
(158) 3-(N-Benzyl-N-methylamino)-2,2-dimethylpropyl methyl 2,6-dimethyl-4-(2-chloro-3-fluorophenyl)-1,4-dihydropyridine-3,5-dicarboxylate
(160) 3-(N-Benzyl-N-methylamino)-2,2-dimethylpropyl ethyl 2,6-dimethyl-4-(2-fluoro-5-nitrophenyl)-1,4-dihydropyridine-3,5-dicarboxylate
(162) 3-(N-Benzyl-N-methylamino)-2,2-dimethylpropyl ethyl 2,6-dimethyl-4-(2-fluoro-3-nitrophenyl)-1,4-dihydropyridine-3,5-dicarboxylate
(164) 3-(N-Benzyl-N-methylamino)-2,2-dimethylpropyl isopropyl 2,6-dimethyl-4-(2-fluoro-3-nitrophenyl)-1,4-dihydropyridine-3,5-dicarboxylate
(166) 2-(N-Benzyl-N-methylamino)ethyl methyl 2,6-dimethyl-4-(2-chloro-6-fluorophenyl)-1,4-dihydropyridine-3,5-dicarboxylate
(168) 3-(N-Benzyl-N-methylamino)-2,2-dimethylpropyl methyl 2,6-dimethyl-4-(2-chloro-6-fluorophenyl)-1,4-dihydropyridine-3,5-dicarboxylate
(170) 3-(N-Benzyl-N-methylamino)-2,2-dimethylpropyl methyl 2-ethyl-6-methyl-4-(2-fluoro-5-nitrophenyl)-1,4-dihydropyridine-3,5-dicarboxylate
(172) 3-(N-Benzyl-N-methylamino)-2,2-dimethylpropyl methyl 2,6-dimethyl-4-(2,5-dichlorophenyl)-1,4-dihydropyridine-3,5-dicarboxylate
(174) 3-(N-Benzyl-N-methylamino)-2,2-dimethylpropyl methyl 2,6-dimethyl-4-(2,6-dichlorophenyl)-1,4-dihydropyridine-3,5-dicarboxylate
(176) 3-(N-Benzyl-N-methylamino)-2,2-dimethylpropyl methyl 2,6-dimethyl-4-(2,3-difluorophenyl)-1,4-dihydropyridine-3,5-dicarboxylate
(178) 3-(N-Benzyl-N-methylamino)-2,2-dimethylpropyl methyl 2,6-dimethyl-4-(2,5-difluorophenyl)-1,4-dihydropyridine-3,5-dicarboxylate
(180) 2-(N-Benzyl-N-methylamino)ethyl methyl 2,6-dimethyl-4-(2,5-difluorophenyl)-1,4-dihydropyridine-3,5-dicarboxylate
(182) 3-(N-benzyl-N-methylamino)-2,2-dimethylpropyl methyl 2,6-dimethyl-4-(2,6-difluorophenyl)-1,4-dihydropyridine-3,5-dicarboxylate
(184) 2-(N-Benzyl-N-methylamino)ethyl methyl 2,6-dimethyl-4-(2-chloro-5-fluorophenyl)-1,4-dihydropyridine-3,5-dicarboxylate
(186) 3-(N-Benzyl-N-methylamino)-2,2-dimethylpropyl methyl 2,6-dimethyl-4-(2-chloro-5-fluorophenyl)-1,4-dihydropyridine-3,5-dicarboxylate
(188) 2-(N-Benzyl-N-methylamino)ethyl methyl 2,6-dimethyl-4-(3-fluoro-2-nitrophenyl)-1,4-dihydropyridine-3,5-dicarboxylate
(190) 3-(N-Benzyl-N-methylamino)-2,2-dimethylpropyl methyl 2,6-dimethyl-4-(3-fluoro-2-nitrophenyl)-1,4-dihydropyridine-3,5-dicarboxylate (192) 3-(N-Benzyl-N-methylamino)-2,2-dimethylpropyl methyl 2,6-dimethyl-4-(5-fluoro-2-nitrophenyl)-1,4-dihydropyridine-3,5-dicarboxylate
(194) 3-(N-Benzyl-N-methylamino)-2,2-dimethylpropyl methyl 2,6-dimethyl-4-(5-chloro-2-nitrophenyl)-1,4-dihydropyridine-3,5-dicarboxylate
(196) 3-(N-Benzyl-N-methylamino)-2,2-dimethylpropyl methyl 2,6-dimethyl-4-(2-chloro-6-nitrophenyl)-1,4-dihydropyridine-3,5-dicarboxylate
(198) 3-(N-Benzyl-N-methylamino)-2,2-dimethylpropyl methyl 2,6-dimethyl-4-(2-fluoro-6-nitrophenyl)-1,4-dihydropyridine-3,5-dicarboxylate
(200) 3-(N-4-Methylbenzyl-N-methylamino)-2,2-dimethylpropyl methyl 2,6-dimethyl-4-(3-chloro-2-fluorophenyl)-1,4-dihydropyridine-3,5-dicarboxylate
(202) 3-(N-2,6-Dichlorobenzyl-N-methylamino)-2,2-dimethylpropyl methyl 2,6-dimethyl-4-(3-chloro-2-fluorophenyl)-1,4-dihydropyridine-3,5-dicarboxylate
(204) 3-(N-Benzyl-N-isopropylamino)-2,2-dimethylpropyl methyl 2,6-dimethyl-4-(3-chloro-2-fluorophenyl)-1,4-dihydropyridine-3,5-dicarboxylate
(206) 3-(N-2-Chlorobenzyl-N-methylamino)-2,2-dimethylpropyl methyl 2,6-dimethyl-4-(2-fluoro-3-nitrophenyl-1,4-dihydropyridine-3,5-dicarboxylate
(208) 3-(N-3-Chlorobenzyl-N-methylamino)-2,2-dimethylpropyl methyl 2,5-dimethyl-4-(2-fluoro-3-nitrophenyl)-1,4-dihydropyridine-3,5-dicarboxylate
(210) 3-(N-Benzyl-N-propylamino)-2,2-dimethylpropyl methyl 2,6-dimethyl-4-(2-fluoro-3-nitrophenyl)-1,4-dihydropyridine-3,5-dicarboxylate
(212) 5-(N-Benzyl-N-methylamino)-3,3-dimethylpentyl methyl 2,6-dimethyl-4-(2-fluoro-3-nitrophenyl)-1,4-dihydropyridine-3,5-dicarboxylate
(214) 3-(N-4-Fluorobenzyl-N-methylamino)-2,2-dimethylpropyl methyl 2,6-dimethyl-4-(2-fluoro-5-nitrophenyl)-1,4-dihydropyridine-3,5-dicarboxylate
(216) 3-(N-3-Fluorobenzyl-N-methylamino)-2,2-dimethylpropyl methyl 2,6-dimethyl-4-(2-fluoro-5-nitrophenyl)-1,4-dihydropyridine-3,5-dicarboxylate
(218) 3-(N-4-Fluorophenethyl-N-methylamino)-2,2-dimethylpropyl methyl 2,6-dimethyl-4-(2-fluoro-5-nitrophenyl)-1,4-dihydropyridine-3,5-dicarboxylate
(220) 3-(N-Benzyl-N-methylamino)-2,2-dimethylpropyl methyl 2,6-diethyl-4-(2-fluoro-5-nitrophenyl)-1,4-dihydropyridine-3,5-dicarboxylate
(222) 3-(N-Benzyl-N-methylamino)-2,2-dimethylpropyl methyl 2,6-dipropyl-4-(2-fluoro-5-nitrophenyl)-1,4-dihydropyridine-3,5-dicarboxylate
(224) 4-(N-Benzyl-N-methylamino)-2,2-dimethylbutyl methyl 2,6-dimethyl-4-(3-chloro-2-fluorophenyl)-1,4-dihydropyridine-3,5-dicarboxylate
(226) 4-(N-Benzyl-N-methylamino)-3,3-dimethylbutyl methyl 2,6-dimethyl-4-(2-chloro-4-nitrophenyl)-1,4-dihydropyridine-3,5-dicarboxylate
(228) 3-(N-Benzyl-N-methylamino)-2,2-diethylpropyl methyl 2,6-dimethyl-4-(2-chloro-3-nitrophenyl)-1,4-dihydropyridine-3,5-dicarboxylate
(230) 2-(N-3,4-Dimethoxybenzyl-N-methylamino)ethyl methyl 2,6-dimethyl-4-(2-chloro-3-nitrophenyl)-1,4-dihydropyridine-3,5-dicarboxylate
(232) 2-(N-Phenethyl-N-methylamino)ethyl methyl 2,6-dimethyl-4-(2-chloro-3-nitrophenyl)-1,4-dihydropyridine-3,5-dicarboxylate
(234) 4-(N-Benzyl-N-methylamino)butyl methyl 2,6-dimethyl-4-(2-chloro-3-nitrophenyl)-1,4-dihydropyridine-3,5-dicarboxylate
(236) 3-(N-3,4-Dimethoxybenzyl-N-methylamino)-2,2-dimethylpropyl methyl 2,6-dimethyl-4-(2-fluoro-3-nitrophenyl)-1,4-dihydropyridine-3,5-dicarboxylate
(238) 3-(N-Phenetyl-N-methylamino)-2,2-dimethylpropyl methyl 2,6-dimethyl-4-(2-fluoro-3-nitrophenyl)-1,4-dihydropyridine-3,5-dicarboxylate
(240) 3-(N-4-Fluorophenethyl-N-methylamino)-2,2-dimethylpropyl methyl 2,6-dimethyl-4-(2-fluoro-3-nitrophenyl)-1,4-dihydropyridine-3,5-dicarboxylate
(242) 3-(N-Benzyl-N-methylamino)-2,2-dimethylpropyl methyl 6-methyl-2-propyl-4-(2-fluoro-3-nitrophenyl)-1,4-dihydropyridine-3,5-dicarboxylate
(244) 3-(N-Benzyl-N-methylamino)-2,2-dimethylpropl methyl 2,6-dipropyl-4-(2-fluoro-3-nitrophenyl)-1,4-dihydropyridine-3,5-dicarboxylate
(246) 3-(N-Benzyl-N-methylamino)-2,2-dimethylpropyyl methyl 2-methyl-6-propyl-4-(2-fluoro-3-nitrophenyl)-1,4-dihydropyridine-3,5-dicarboxylate
(248) 3-(N-Benzyl-N-methylamino)-2,2-dimethylpropyl methyl 1,2,6-trimethyl-4-(2-fluoro-3-nitrophenyl)-1,4-dihydropyridine-3,5-dicarboxylate
(250) 2-(N-4-Methylphenethyl-N-methylamino)ethyl methyl 2,6-dimethyl-4-(2-fluoro-3-nitrophenyl)-1,4-dihydropyridine-3,5-dicarboxylate
(252) 2-(N-4-Methoxyphenethyl-N-methylamino)ethyl methyl (2,6-dimethyl-4-(2-fluoro-3-nitrophenyl)-1,4-dihydropyridine-3,5-dicarboxylate
(254) 2-(N-Benzyl-N-methylamino)ethyl methyl 1-ethyl-2,6-dimethyl-4-(2-fluoro-3-nitrophenyl)-1,4-dihydropyridine-3,5-dicarboxylate
(256) 2-(N-Benzyl-N-methylamino)ethyl methyl 6-ethyl-2-methyl-4-(2-fluoro-3-nitrophenyl)-1,4-dihydropyridine-3,5-dicarboxylate
(258) 3-(N-Benzyl-N-methylamino)propyl methyl 2,6-dimethyl-4-(2-fluoro-3-nitrophenyl)-1,4-dihydropyridine-3,5-dicarboxylate
(260) 2-(N-4-Methoxyphenethyl-N-methylamino)ethyl methyl 2,6-dimethyl-4-(2-chloro-5-nitrophenyl)-1,4-dihydropyridine-3,5-dicarboxylate
(262) 2-(N-Benzyl-N-methylamino)ethyl methyl 1,2,6-trimethyl-4-(2-chloro-5-nitrophenyl)-1,4-dihydropyridine-3,5-dicarboxylate
(264) 4-(N-Benzyl-N-methylamino)butyl methyl 2,6-dimethyl-4-(2-chloro-5-nitrophenyl)-1,4-dihydropyridine-3,5-dicarboxylate
(266) 2-(N-Benzyl-N-methylamino)ethyl methyl 2-methyl-6-propyl-4-(2-chloro-5-nitrophenyl)-1,4-dihydropyridine-3,5-dicarboxylate
(268) 2-(N-4-Methylbenzyl-N-methylamino)ethyl methyl 2,6-dimethyl-4-(2-chloro-5-nitrophenyl)-1,4-dihydropyridine-3,5-dicarboxylate
(270) 2-(N-3,4-Dimethoxybenzyl-N-methylamino)ethyl methyl 2,6-dimethyl-4-(2-chloro-5-nitrophenyl)-1,4-dihyropyridine-3,5-dicarboxylate
(272) 3-(N-Phenethyl-N-isopropylamino)-2,2-dimethylpropyl methyl 2,6-dimethyl-4-(2-chloro-5-nitrophenyl)-1,4-dihydropyridine-3,5-dicarboxylate
(274) 3-(N-3,4-Dimethoxybenzyl-N-methylamino)-2,2-dimethylpropyl methyl 2,6-dimethyl-4-(2-fluoro-5-nitrophenyl)-1,4-dihydropyridine-3,5-dicarboxylate
(276) 4-(N-Benzyl-N-methylamino)-3,3-dimethylbutyl methyl 2,6-dimethyl-4-(2-fluoro-5-nitrophenyl)-1,4-dihydropyridine-3,5-dicarboxylate
(278) 5-(N-Benzyl-N-methylamino)-3,3-dimethylpentyl methyl 2,6-dimethyl-4-(2-fluoro-5-nitrophenyl)-1,4-dihydropyridine-3,5-dicarboxylate (280) 3-(N-Benzyl-N-isopropylamino)-2,2-dimethylpropyl methyl 2,6-dimethl-4-(2-fluoro-5-nitrophenyl)-1,4-dihydropyridine-3,5-dicarboxylate (282) 3-(N-4-Trifluoromethylbenzyl-N-methylamino)-2,2-dimethylpropyl methyl 2,6-dimethyl-4-(2-fluoro-5-nitrophenyl)-1,4-dihydropyridine-3,5-dicarboxylate (284) 2-(N-Benzyl-N-methylamino)ethyl propyl 2,6-dimethyl-4-(2-fluoro-4-nitrophenyl)-1,4-dihydropyridine-3,5-dicarboxylate (286) 3-(N-4-Fluorobenzyl-N-methylamino)-2,2-dimethylpropyl methyl 2,6-dimethyl-4-(3-chloro-2-fluorophenyl)-1,4-dihydropyridine-3,5-dicarboxylate (288) 3-(N-4-Methoxybenzyl-N-methylamino)-2,2-dimethylpropyl methyl 2,6-dimethyl-4-(3-chloro-2-fluorophenyl)-1,4-dihydropyridine-3,5-dicarboxylate (290) 3-(N-2,3-Dichlorobenzyl-N-methylamino)-2,2-dimethylpropyl methyl 2,6-dimethyl-4-(2-fluoro-5-nitrophenyl)-1,4-dihydropyridine-3,5-dicarboxylate Compounds of formula [1]-b (300) 3-(N-Benzyl-N-methylamino)-2,2-dimethylpropyl methyl 2,6-dimethyl-4-(2-nitrophenyl)-1,4-dihydropyridine-3,5-dicarboxylate (302) 3-(N-Benzyl-N-methylamino)-2,2-dimethylpropyl methyl 2,6-dimethyl-4-(3-nitrophenyl)-1,4-dihydropyridine-3,5-dicarboxylate (304) 3-(N-Benzyl-N-methylamino)-2,2-dimethylpropyl methyl 2,6-dimethyl-4-(3-fluorophenyl)-1,4-dihydropyridine-3,5-dicarboxylate (306) 3-(N-Benzyl-N-methylamino)-2,2-diethylpropyl methyl 2,6-dimethyl-4-(2-nitrophenyl)-1,4-dihydropyridine-3,5-dicarboxylate (308) 4-(N-Benzyl-N-ethylamino)-2,2-dimethylbutyl ethyl 2,6-dimethyl-4-(2-nitrophenyl)-1,4-dihydropyridine-3,5-dicarboxylate (310) 3-(N-Benzyl-N-methylamino)-2,2-dimethylpropyl methyl 2,6-dimethyl-4-(2-fluorophenyl)-1,4-dihydropyridine-3,5-dicarboxylate (312) 3-(N-Benzyl-N-methylamino)-2,2-dimethylpropyl isopropyl 2,6-dimethyl-4-(2-fluorophenyl)-1,4-dihydropyridine-3,5-dicarboxylate (314) 4-(N-Benzyl-N-methylamino)-2,2-dimethylpropyl methyl 1,2,6-trimethyl-4-(2-fluorophenyl)-1,4-dihydropyridine-3,5-dicarboxylate (316) 4-(N-Benzyl-N-methylamino)-2,2-dimethylbutyl methyl 2,6-dimethyl-4-(3-nitrophenyl)-1,4-dihydropyridine-3,5-dicarboxylate (318) 4-(N-Benzyl-N-methylamino)-3,3-dimethylbutyl methyl 2,6-dimethyl-4-(3-nitrophenyl)-1,4-dihydropyridine-3,5-dicarboxylate (320) 5-(N-Benzyl-N-methylamino)-3,3-dimethylpentyl methyl 2,6-dimethyl-4-(3-nitrophenyl)-1,4-dihydropyridine-3,5-dicarboxylate (322) 3-(N-Benzyl-N-propylamino)-2,2-dimethylpropyl methyl 2,6-dimethyl-4-(3-nitrophenyl)-1,4-dihydropyridine-3,5-dicarboxylate (324) 3-(N-Benzyl-N-methylamino)-2,2-dimethylpropyl methyl 2,6-dipropyl-4-(3-nitrophenyl)-1,4-dihydropyridine-3,5-dicarboxylate (326) 3-(N-4-Fluorobenzyl-N-methylamino)-2,2-dimethylpropyl methyl 2,6-dimethyl-4-(3-fluorophenyl)-1,4-dihydropyridine-3,5-dicarboxylate (328) 3-(N-3-Methoxybenzyl-N-methylamino)-2,2-dimethylpropyl methyl 2,6-dimethyl-4-(3-fluorophenyl)-1,4-dihydropyridine-3,5-dicarboxylate (330) 3-(N-2,6-Dichlorobenzyl-N-methylamino)-2,2-dimethylpropyl methyl 2,6-dimethyl-4-(3-fluorophenyl)-1,4-dihydropyridine-3,5-dicarboxylate (332) 3-(N-4-Methylbenzyl-N-methylamino)-2,2-dimethylpropyl methyl 2,6-dimethyl-4-(3-fluorophenyl)-1,4-dihydropyridine-3,5-dicarboxylate (334) 3-(N-3,4-Dimethoxybenzyl-N-methylamino)-2,2-dimethylpropyl methyl 2,6-dimethyl-4-(3-nitrophenyl)-1,4-dihydropyridine-3,5-dicarboxylate (336) 3-(N-4-Trifluoromethylbenzyl-N-methylamino)-2,2-dimethylpropyl methyl 2,6-dimethyl-4-(3-nitrophenyl)-1,4-dihydropyridine-3,5-dicarboxylate (338) 3-(N-Phenethyl-N-methylamino)-2,2-dimethylpropyl methyl 2,6-dimethyl-4-(3-nitrophenyl)-1,4-dihydropyridine-3,5-dicarboxylate (340) 3-(N-4-Methoxyphenethyl-N-methylamino)-2,2-dimethylpropyl methyl 2,6-dimethyl-4-(3-nitrophenyl)-1,4-dihydropyridine-3,5-dicarboxylate (342) 3-(N-4-Methylbenzyl-N-methylamino)-2,2-dimethylpropyl methyl 2,6-dimethyl-4-(3-nitrophenyl)-1,4-dihydropyridine-3,5-dicarboxylate (344) 3-(N-Benzyl-N-methylamino)-2,2-dimethylpropyl methyl 6-ethyl-2-methyl-4-(3-nitrophenyl)-1,4-dihydropyridine-3,5-dicarboxylate (346) 3-(N-Benzyl-N-methylamino)-2,2-dimethylpropyl methyl 6-methyl-2-propyl-4-(3-nitrophenyl)-1,4-dihydropyridine-3,5-dicarboxylate (348) 3-(N-Benzyl-N-methylamino)-2,2-dimethylpropyl methyl 2,6-dimethyl-4-(3-chlorophenyl)-1,4-dihydropyridine-3,5-dicarboxylate (350) 3-(N-Benzyl-N-methylamino)-2,2-dimethylpropyl methyl 2,6-dimethyl-4-(2-chlorophenyl)-1,4-dihydropyridine-3,5-dicarboxylate In Examples to be given hereinbelow, the compounds of the invention are designated by the number in palentheses attached in the above exemplification. The hydrochloride of compound (100), for example, is reffered to as (100) hydrochloride.

The process for producing the 1,4-dihydropyridine derivative of this invention is described below in detail.

The 1,4-dihydropyridine derivative of this invention can be produced according to various methods (Reaction Schemes A to H) mentioned below, the details of which are explained in the following.

Reaction Scheme A

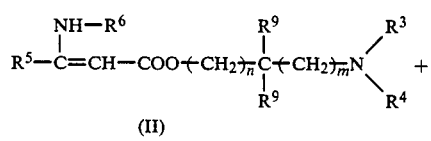

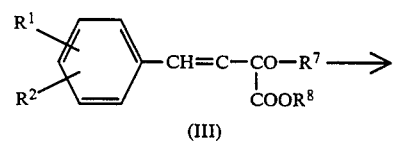

-continued
Reaction Scheme A

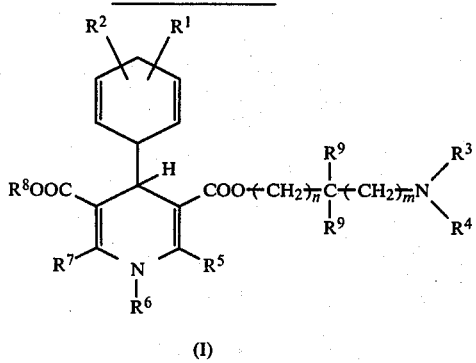

(I)

In the Reaction Scheme A, the enaminocarboxylate derivative of the formula (II) is made to react with the α-benzylidene-β-ketoester derivative of the formula (III). The reaction product is then subjected to a salt-forming reaction, if required.

In the formula (II), $R^3$, $R^4$, $R^5$, $R^6$, $R^9$, n and m are as defined in the formula (I). In the formula (III), $R^1$, $R^2$, $R^7$ and $R^8$ are as defined in the formula (1).

The enaminocarboxylate derivative of the aforementioned formula (II) can be produced from a proper acetoacetate derivative and a proper amine compound according to a known method (Chem. Pharm. Bull., vol. 27, 1926 (1979); J.A.C.S., 67, 1017 (1945)).

The α-benzylidene-β-ketoester derivative of the aforementioned formula (III) can be produced from a proper benzaldehyde compound and a proper acetoacetate derivative according to a known method (Chem. Ber. vol. 31, 730 (1898); Arzneim. Forsch., vol. 31, 407 (1981)).

The reaction of the enaminocarboxylate derivative of said formula (II) with the α-benzylidene-β-ketoester derivative of said formula (III) is carried out in a solvent or without the use of a solvent and, if required, in the presence of a basic compound, by application of heat.

Examples of the solvent involve such lower alkyl alchols as methanol, ethanol, propanol, 2-propanol, n-butanol and tert-butanol; such halogenated hydrocarbons as dichloromethane, chloroform, 1,2-dichloroethane and trichloroethane; such aromatic hydrocarbons as benzene, toluene, xylene and pyridine; such ethers as dioxane, diethylether and tetrahydrofutane; and dimethylsulforide and dimethylform amide and dimethyl acetonid.

Mixtures of these solvents may be used and these solvents may contain water.

The reaction temperature ranges from 30° C. to 180° C., preferably from 50° C. to 150° C. The reaction time varies depending upon the reaction temperature, the amount of reagent and the solvent used, etc.; however, it is usually in the range of about 1 to 24 hours.

The enaminocarboxylate derivative of the formula (II) may be used in an amount of 0.8 to 1.5 moles per mole of the α-benzylidene-β-ketoester derivative of the formula (III).

It may be possible to carry out the reaction in the presence of a basic compound. Examples of the basic compound include such tertiary amines as triethylamine, tri-propylamine, N,N-dimethylaniline, N-methylmorpholine, N-methylpyperidine and pyridine. The basic compound may be used in an amount of 0.1 to 2.0 moles per mole of the enaminocarboxylate derivative of the formula (II).

The separation of the desired product from the resulting reaction mixture and its purification can be carried out by extraction, crystallization, column chromatography, etc.

The desired product may be purified after the reaction product is subjected to a salt-forming reaction.

The salt-forming reaction is known per se, and can be carried out by neutralizing the 1,4-dihydropyridine derivative having an amino group with the acid described above in such ethers as diethylether and tetrahydrofurane; such alchols as methanol, ethanol, propanol and 2-propanol; such hydrocarbons as benzene, toluene and xylene; or alchols containing water.

Reaction Scheme B

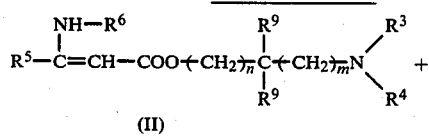

(II)

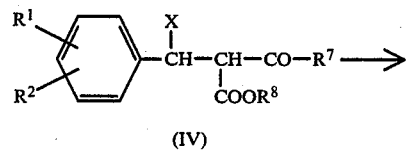

(IV)

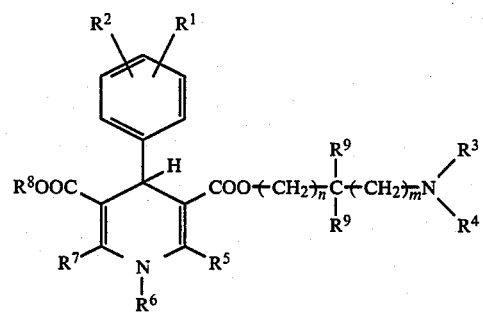

(I)

In the Reaction Scheme B, the enaminocarboxylate derivative of the formula (II) is allowed to react with the α-halobenzyl-β-ketoester derivative of the formula (IV). The reaction product is then subjected to a salt-forming reaction, if required.

In the formula (IV), X represents a halogen atom.

Examples of the halogen atom include chlorine, fluorine, bromine, and idoine atom, of which chlorine atom is preferable. In the formula (IV), $R^1$, $R^2$, $R^7$ and $R^8$ are as defined in the formula (I).

The α-halobenzyl-β-ketoester derivative of the aforementioned formula (IV) can be produced by allowing benzaldehydes expressed by the following formula (IV-a)

(IV-a)

wherein $R^1$ and $R^2$ are as defined above, to react with β-ketoester derivative expressed by the following formula (IV-b)

$$R^7-CO-CH_2-COOR^8 \qquad (IV\text{-}b)$$

wherein $R^7$ and $R^8$ are as defined above, in the presence of such hydrogen halogenides as hydrogen chloride, etc. in such nonaqueous organic solvents as benzene, toluene, xylene, etc. or without the use of a solvent at a temperature ranging from −30° C. to 100° C. for 1 to 24 hours.

The reaction of the enaminocarboxylate derivative of the aforementioned formula (II) with the α-halobenzyl-β-ketoester derivative of the aforementioned formula (IV) is conducted without a solvent or in a solvent, and in the presence of a basic compound, if required, by application of heat.

The solvents and basic compounds to be used here and the reaction conditions including the reaction temperature, etc. are almost the same as the Reaction Scheme A. The salt-forming reaction can also be conducted in the same way as the Reaction Scheme A.

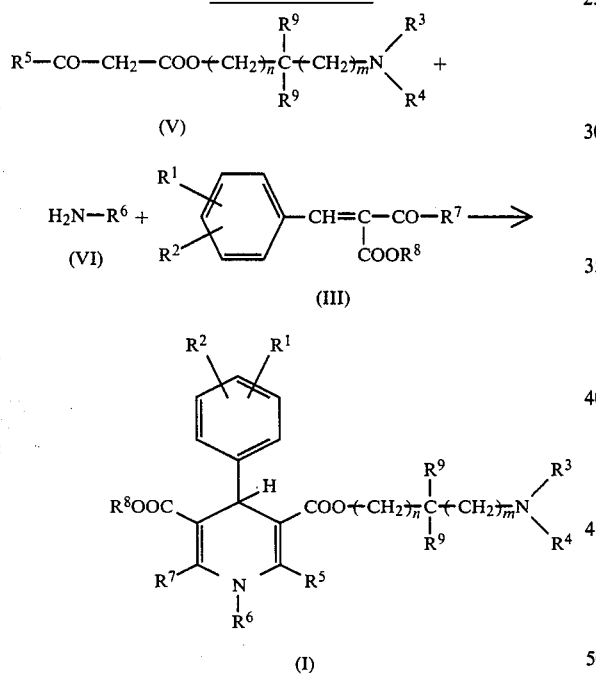

In the Reaction Scheme C, the β-ketoester derivative of the formula (V), the amine compound of the formula (VI) and the α-benzylidene-β-ketoester derivative of the formula (III) are made to react with each other.

The reaction product is then subjected to a salt-forming reaction, if required.

In the formula (V), $R^3$, $R^4$, $R^5$, $R^9$, n and m are as defined in the formula (I). In the formula (VI), $R^6$ is as defined in the formula (I).

The β-ketoester derivative ($R^5$=methyl) of the aforementioned formula (V) can be produced by allowing a proper alcohol to react with diketene according to a publicly known method (Chemical Abstracts, 50, 16668h (1956); Organic Synthesis, vol. 42, 28; Chem. Pharm. Bull., vol. 27, 1426 (1979)). The β-ketoester derivative ($R^5$=other alkyl group) can be produced according to the method disclosed in U.S. Pat. No. 2,351,366. The amine compound of the aforementioned formula (VI) is a publicly known compound.

The reaction of the β-ketoester derivative of said formula (V) with the amine compound of said formula (VI) and the α-halobenzyl-β-ketoester derivative of said formula (III) is conducted in a solvent or without a solvent, and in the presence of a basic compound, if required, by application of heat. The compound of the formula (V) may be used in an amount of 0.8 to 1.5 moles per moles of the compound of the formula (III). The amine compound of the formula (VI) may be used in an amount of 0.8 to 1.5 moles or more per moles of the compound of the formula (III). The solvents and basic compounds to be used in this reaction and the reaction conditions including the reaction temperature, etc. are almost the same as the Reaction Scheme A. The salt-forming reaction can also be conducted in the same way as the Reaction Scheme A.

Incidentally, there is another process for obtaining the desired 1,4-dihydropyridine derivative of the formula (I), wherein the amine compound of the aforementioned formula (VI) is made to react with the β-ketoester derivative of the aforementioned formula (V) to give the enaminocarboxylate derivative of the formula (II) of the Reaction Scheme A, which is then allowed to react with the α-halobenzyl-β-ketoester acetate derivative of the formula (III) according to the same way as the Reaction Scheme A.

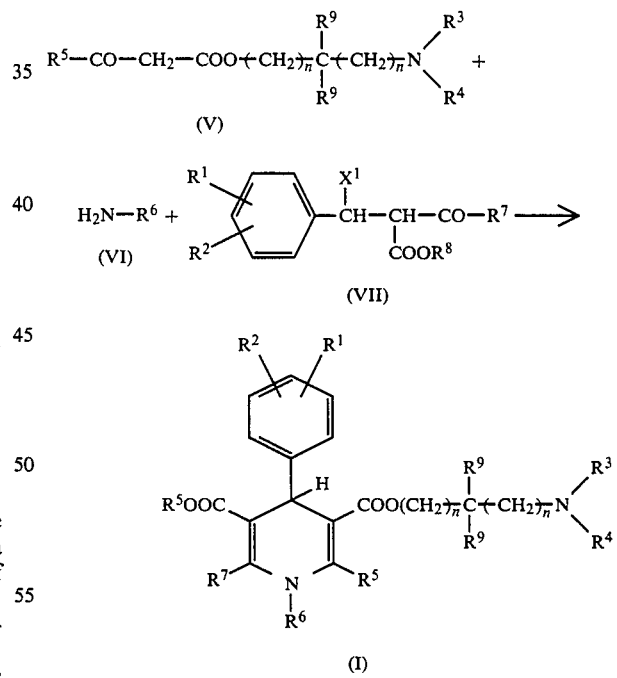

In the Reaction Scheme C, the β-ketoester derivative of the formula (V), the amino compound of the formula (VI) and the α-halogenobenzyl-β-ketoester derivative of the formula (VII) are made to react with each other. The reaction product is then subjected to a salt-forming reaction, if required.

In the formula (VII), $X^1$ represents a halogen atom. Examples of the halogen atom include chlorine, fluorine, bromine, and iodine atomm.

The α-halogenobenzyl-β-ketoester derivatives of the formula (VII) can be produced by the same way as Reaction Scheme B.

The reaction of the β-ketoester derivative of said formula (V) with the amine compound of said formula (VI) and the α-halogenobenzyl-β-ketoester derivative of said formula (VII) is conducted in a solvent or without a solvent, and in the presence of a basic compound, if required, by application of heat.

The solvent and basic compounds to be used here and the reaction conditions including the reaction temperature, etc. are almost the same as the Reaction Scheme C. The salt-forming reaction can also be conducted in the same way as the Reaction Scheme A.

Reaction Scheme E

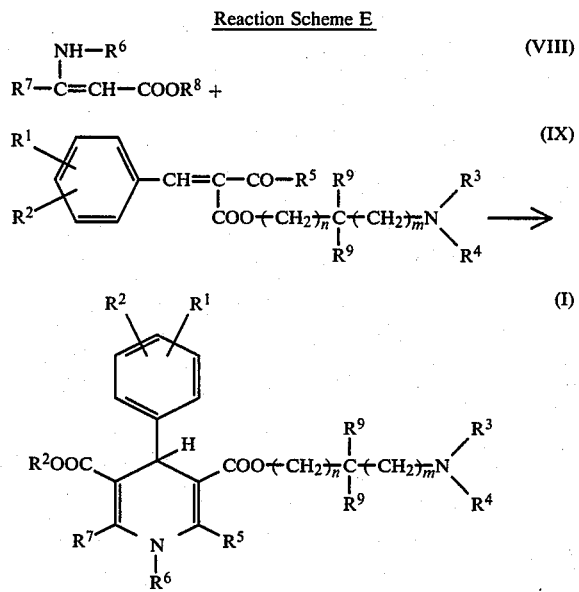

In the Reaction Scheme E, the enaminocaroboxylate derivative of the formula (VIII) is made to react with the α-benzylidene-β-ketoester derivative of the formula (IX). The reaction product is then subjected to a salt-forming reaction, if required.

The enaminocaroboxylate derivative of the above-mentioned formula (VIII) can be produced from a proper acetoacetic acid ester derivative and a proper amine compound according to a known method (Chem. Pharm. Bull., vol. 27, 1426 (1979); J.A.C.S., 67, 1017 (1945)).

Also, the α-benzylidene-β-ketoester derivative of the abovementioned formula (IX) can be prepared from a proper benzaldehyde compound and a proper acetoacetate derivative according to a known method (Chem. Ber., vol. 31, 730 (1898); Arzneim. Forsch., vol. 31, 407 (1981)).

The reaction of the enaminocaroboxylate derivative of the abovementioned formula (VIII) with the α-benzylidene-β-ketoester derivative of the abovementioned formula (IX) is carried out in a solvent or without using a solvent, and in the presence of a basic compound, if required, by application of heat.

The solvents and basic compounds to be used in the above-mentioned reaction and the reaction conditions including the the reaction temperature, etc. are almost the same as the Reaction Scheme A. The salt-forming reaction can also be conducted in the same way as the Reaction Scheme A.

Reaction Scheme F

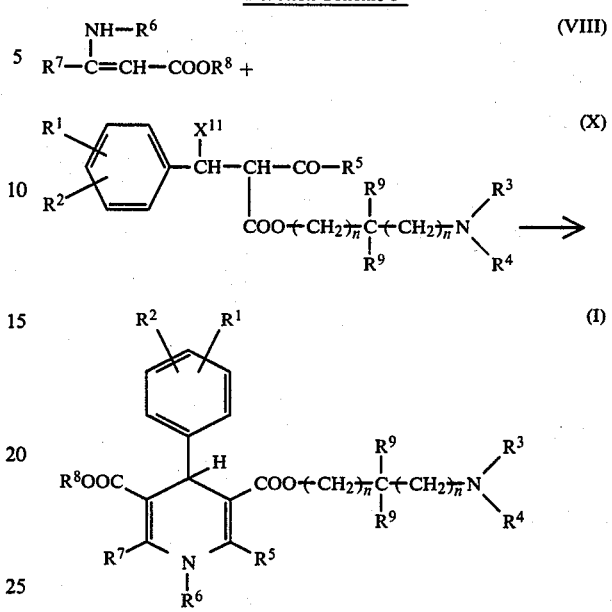

In the Reaction Scheme F, the enaminocarboxylate derivative of the formula (VIII) is made to react with the α-halobenzyl-β-ketoester derivative of the formula (X). The reaction product is then subjected to a salt-forming reaction, if required.

The α-halobenzyl-β-ketoester derivative of the formula (X) can be produced by the same way as Reaction Scheme B.

In the formula (X), $X^{11}$ represents a halogen atom. Examples of the halogen atom include chlorine, fluorine, bromine, and idoine atom.

The reaction of the enaminocarboxylate derivative of the abovementioned formula (VIII) with the α-halobenzyl-β-ketoester derivative of the abovementioned formula (X) is carried out in a solvent or without using a solvent, and in the presence of a basic compound, if required, by application of heat.

The solvents and basic compounds to be used in the abovementioned reaction and the reaction conditions including the reaction temperature, etc. are almost the same as the Reaction Scheme A. The salt-forming reaction can also be conducted in the same way as the Reaction Scheme A.

Reaction Scheme G

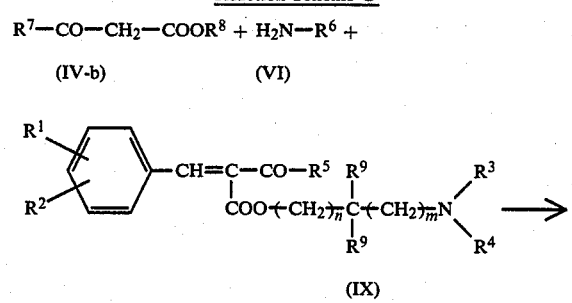

-continued
Reaction Scheme G

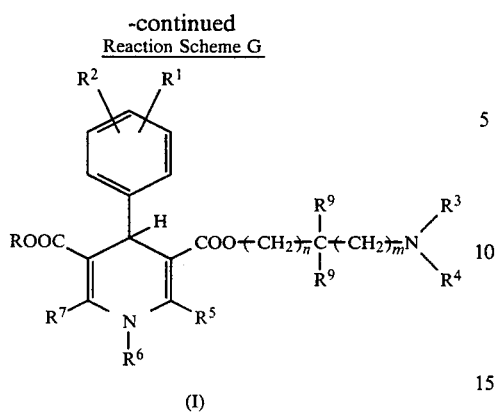

(I)

In the Reaction Schem G, the β-ketoester derivative of the formula (IV-b), the amine compound of the formula (VI) and the α-benzylidene-β-ketoester derivative of the formula (IX) are made to react with each other. The reaction product, if required, is further subjected to a salt-forming reaction.

In the formula (IV-b), $R^7$ and $R^8$ are as defined above. The β-ketoester derivative of the formula (IV-b) is a publicly known compound.

The reaction of the β-ketoester derivative of the aforementioned formula (IV-b) with the amine compound of the aforementioned formula (VI) and the α-benzylidene-β-ketoester derivative of the aforementioned formula (IX) is conducted with or without using a solvent, and in the presence of a basic compound, if required, while heating the reaction mixture. The compound of the formula (IV-b) may be used in an amount of 0.8 to 1.5 moles per moles of the compound of the formula (IV). The compound of the formula (VI) may be used in an amount of 0.5 to 1.5 moles or more per moles of the compound of the formula (IV). The solvents and basic compounds to be used here and the reaction conditions such as the reaction temperature, etc. are almost the same as the Reaction Scheme A. The salt-forming reaction can also be conducted in the same way as the Reaction Scheme A.

The desired 1,4-dihydropyridine derivative can be obtained by first allowing the amine compound of said formula (VI) to react with the β-ketoester derivative of said formula (IV-b) to obtain the enaminocarboxylate derivative of the formula (VIII) which is used in the Reaction Scheme D, which derivative is then made to react with the α-benzylidene-β-ketoester derivative of the aforementioned formula (IX) in the same way as the Reaction Scheme E. The salt-forming reaction can be conducted in the same way as the Reaction Scheme A.

-continued
Reaction Scheme H

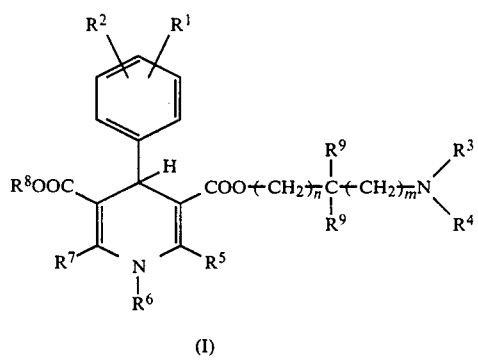

(I)

In the Reaction Scheme H, the β-ketoester derivative of the formula (IV-b), the amine compound of the formula (VI) and the α-halobenzyl-β-ketoester derivative of the formula (XI) are made to react with each other. The reaction product, if required, is further subjected to a salt-forming reaction.

In the formula (XI), $X^{111}$ represents a halogen atom, Examples of the halogen atom include chlorine, fluorine, bromine and iodine atom. The α-halobenzyl-β-ketoester derivative of the formula (XI) can be produced by the same way as Reaction Scheme B.

The reaction of the β-ketoester derivative of the aforementioned formula (IV-b) with the amine compound of the aforementioned formula (VI) and the α-halobenzyl-β-ketoester derivative of the aforementioned formula (XI) is conducted with or without using a solvent, and in the presence of a basic compound, if required, while heating the reaction mixture.

The amount of the compounds, the solvents and basic compounds to be used here and the reaction conditions such as the reaction temperature, etc. are almost the same as the Reaction Scheme A. The salt-forming reaction can also be conducted in the same way as the Reaction Scheme A or G. The salt forming reaction can also be conducted in the same way as the Reaction Scheme A.

Reaction Scheme H $R^7$—CO—$CH_2$—$COOR^8$ + $H_2N$—$R^6$ +

(IV-b)    (VI)

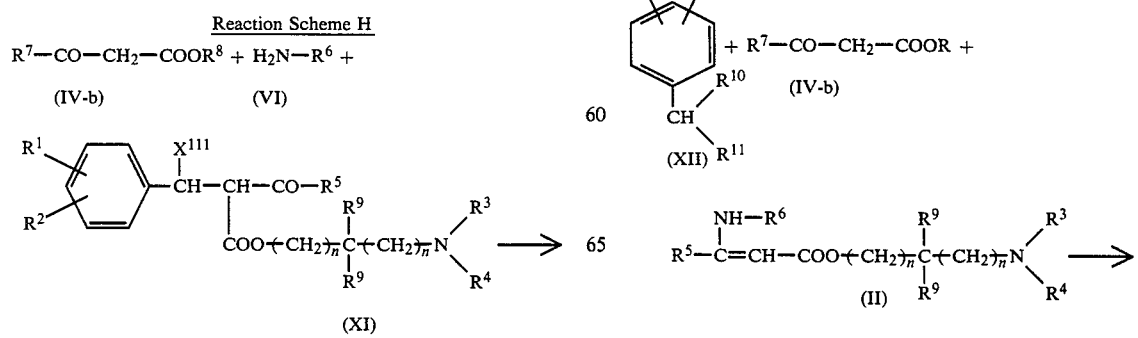

-continued
Reaction Scheme I

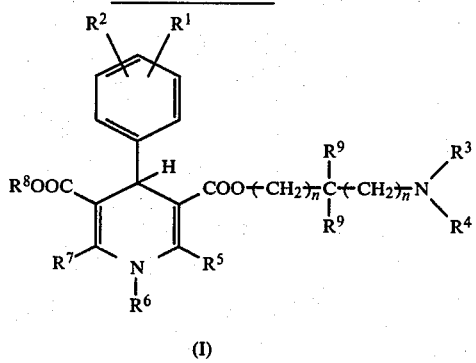

(I)

In the Reaction Scheme I, the benzaldehyde derivative of the formula (XII), the β-ketoester derivative of the formula (IV-b), and the enaminocarboxylate derivative of the formula (II) are allowed to react with each other. The reaction product, if required, is further subjected to a salt-forming reaction.

In the formula (XII), $R^{10}$ and $R^{11}$ are identical, each representing a halogen atom an acyloxy group or an alkoxy group; or $R^{10}$ and $R^{11}$ may together form an oxo group (=O), and $R^1$ and $R^2$ are as defined in the formula (I).

Examples of suitable halogen atoms include fluorine, chlorine and bromine atoms.

Examples of suitable acyloxy groups include $C_1$-$C_6$ acyloxy group such as acetoxy, propionyloxy, n-butyrylary, iso-butyryloxy and n-valeryloxy.

Examples of suitable alkoxy groups include $C_1$-$C_6$ alkoxy group such as methoxy, ethoxy, n-propoxy and n-butoxy.

The benzaldehyde derivative of the abovementioned formula (XII), in which $R^{10}$ and $R^{11}$ together form an oxo group, can be produced according to a known method (Organic Reactions, VIII, 218 ff (1954)). For instance, it can be obtained by oxidizing a proper toluene derivative or a hydroxymethyl benzene derivative by use of such oxidizing agents as manganese dioxide, chromic acid, silver oxide, cerium nitrate, etc. The benzaldehyde derivative of the abovementioned formula (XII), in which $R^{10}$ and $R^{11}$ are halogen atoms, can be produced according to a known method. It can be produced by reacting a proper toluene derivative with diethyl oxalate and sodium hypochlorite, or by reacting a proper toluene derivative with sodium N-bromosuccinate. The benzaldehyde derivative of the formula (XII), in which $R^{10}$ and $R^{11}$ are acyloxy groups, can be produced by oxidizing a proper toluene derivative in the presence of carboxylic acid anhydride (Organic Synthesis, vol. 4, 713, 1963).

The benzaldehyde derivative of the formula (XII), in which $R^{10}$ and $R^{11}$ are alkoxy groups, can be produced by reacting the benzaldehyde derivative of the formula (XII) in which $R^{10}$ and $R^{11}$ are acyloxy group with an alcohol.

The reaction of the benzaldehyde derivative of the formula (XII) with the β-ketoester derivative of the formula (IV-b) and the enaminocarboxylate derivative of the formula (II) is conducted with or without the use of a solvent, and in the presence of a basic compound, if required, by application of heat.

As examples of the solvent, there are such lower alkyl alcohols as methanol, ethanol, propanol, 2-propanol, n-butanol and tert-butanol; such halogenated hydrocarbons as dichloromethane, chloroform, 1,2-dichloroethane and trichloroethane; such aromatic hydrocarbons as benzene, toluene, xylene and pyridine; and such ethers as dimethylether, diethylether and dipropyl ether. The mixtures of these solvents may be used, and these solvents may contain water.

The reaction temperature is from 30° C. to 180° C., preferably from 50° C. to 150° C. The reaction time varies depending upon the reaction temperature, the amount of reagent and the solvent used, etc. Usually, it is about 2 to 24 hours.

The β-ketoester derivative of the formula (IV-b) and the enaminocarboxylate derivative of the formula (II) may be used respectively in an amount of 0.8 to 1.5 moles per mole of the benzaldehyde derivative of the formula (XII).

In case where the benzaldehyde derivative of the formula (XII), in which $R^{10}$ and $R^{11}$ are identical, respectively representing a halogen atom, is to be used in the reaction, it is preferable to carry out the reaction in the presence of a basic compound. Examples of the basic compound include such tertiary amines as triethylamine, trimethylamine, triethylenediamine, hexamethylenetetramine, N,N-dimethylaniline, N-methylmorpholine, N-methylpiperidine and pyridine. The basic compound may be used in an amount of more than 0.1 moles, preferably more than 2 moles per mole of the benzaldehyde derivative of the formula (XII).

The desired final compound can be isolated and purified, for instance, by extraction, crystallization, chromatography, etc.

The obtained product may be subjected to a salt-forming reaction, if required. The salt-forming reaction can be carried out in the same way as described in the above with regard to the Reaction Scheme A.

Reaction Scheme J

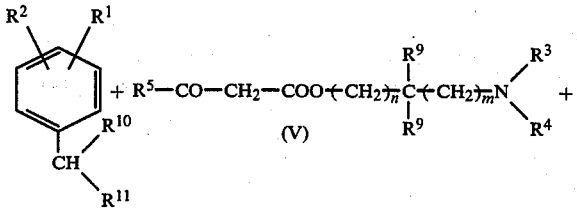

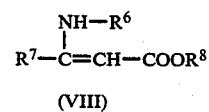

(VIII)

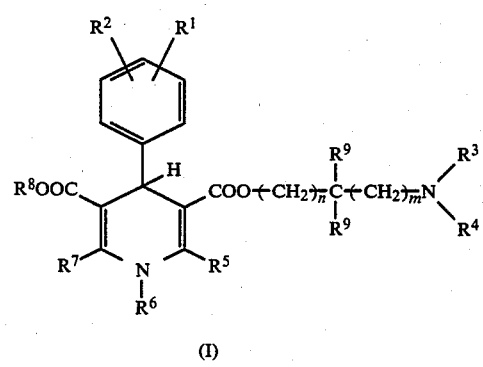

(I)

In the Reaction Schme J, the benzaldehyde derivative of the formula (XII), the β-ketoester derivative of the formula (V), and the enaminocarboxylate derivative of the formula (VIII) are reacted with each other. The reaction product may further be subjected to a salt-forming reaction, if required.

The reaction of the benzaldehyde derivative of the formula (XII) with the β-ketoester derivative of the formula (V) and the enaminocarboxylate derivative of the formula (VIII) is carried out with or without the use of a solvent, and in the presence of a basic compound, if required, by application of heat.

The solvent and basic compound to be used here and the reaction conditions including the reaction temperature, etc. are almost the same as the Reaction Scheme F.

The salt-forming reaction is the same as the Reaction Scheme A.

Reaction Scheme K

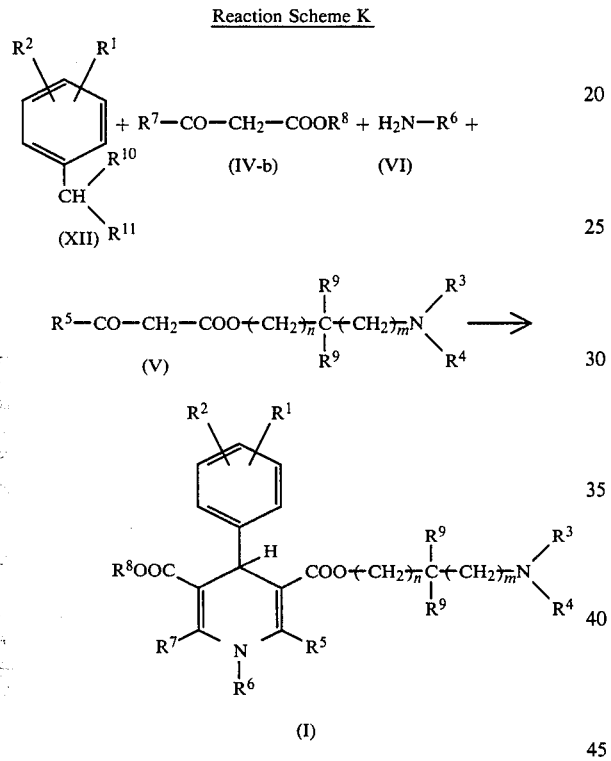

In the Reaction Scheme K, the benzaldehyde derivative of the formula (XII), the β-ketoester derivative of the formula (V), the β-ketoester derivative of the formula (IV-b) and the amine compound of the formula (VI) are reacted with each other. The reaction product may further be subjected to a salt-forming reaction, if required.

The reaction of the benzaldehyde derivative of the formula (XII) with the β-ketoester derivative of the formula (v), the β-ketoester derivative of the formula (IV-b) and the amine compound of the formula (VI) is conducted with or without the use of a solvent, and in the presence of a basic compound, if required, by application of heat.

The β-ketoester derivative of the formula (IV-b) and the β-ketoester derivative of the formula (V) may be used respectively in an amount of 0.8 to 1.5 moles per moles of the benzaldehyde derivative of the formula (XII). The amine compound of the formual (VI) may be used in an amount of 0.8 to 1.5 moles or more per moles of the benzaldehyde derivative of the formula (XII).

The solvents and basic compound to be used here and the reaction conditions such as the reaction temperature, etc. are almost the same as the Reaction Scheme I. The salt-forming reaction can also be conducted in the same way as the Reaction Schem A.

The desired 1,4-dihydropyridine derivative can be obtained by first allowing the amine compound of the formula (VI) to react with the β-ketoester derivative of the formula (IV-b) to obtain the enaminocarboxylate derivative of the formula (VIII) which is used in the Reaction Scheme J, which derivative is then made to react with the benzaldehyde derivative of the formula (XIII) and the β-ketoester derivative of the formula (V) in the same way as Reaction Scheme J.

Reaction Scheme L

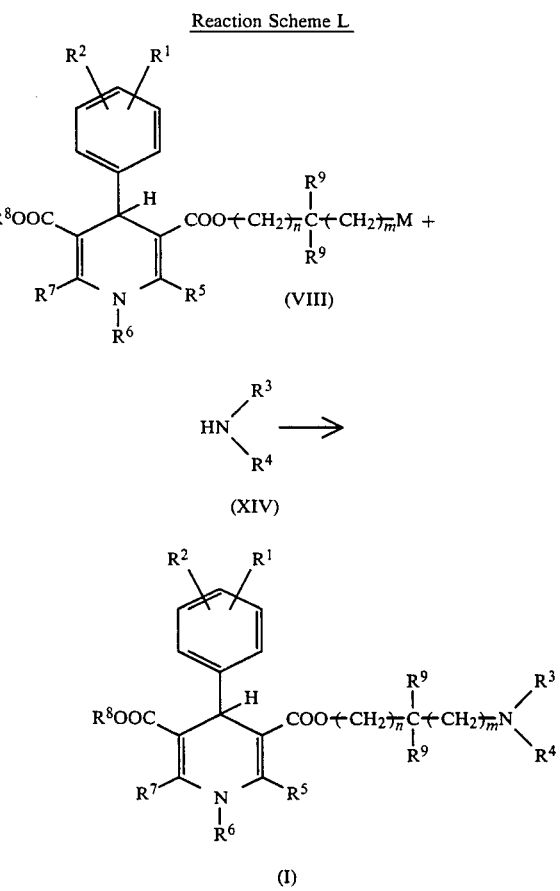

In the Reaction Scheme H, the 1,4-dihydropyridine derivative of the formula (XIII) is made to react with the amine compound of the formula (XIV). The reaction product is then subjected to a salt-forming reaction, if required.

In the formula (XIII), M represents a halogen atom, an alkylsulfonyloxy group or an arylsulfonyloxy group. As examples of halogen atom, there are chlorine, fluorine, and bromine atom. Examples of alkylsulfonyloxy group include methylsulfonyloxy, ethylsulfonyloxy, and propylsulfonyloxy. Examples of arylsulfonyloxy group include benzenesulfonyloxy and p-toluenesulfonyloxy. In the formula (XI), $R^1$, $R^2$, $R^5$, $R^6$, $R^7$, $R^8$, $R^9$, n and m are as defined in the formula (I). The 1,4-dihydropridine derivative of the aforementioned formula (XIII) can be produced from a compound expressed by the following formula (XIII)-a

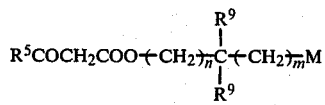

$$\text{R}^5\text{COCH}_2\text{COO}\mathord{\leftarrow}\text{CH}_2\mathord{\rightarrow}_{\overline{n}}\overset{\overset{\text{R}^9}{|}}{\underset{\underset{\text{R}^9}{|}}{\text{C}}}\mathord{\leftarrow}\text{CH}_2\mathord{\rightarrow}_{\overline{m}}\text{M} \qquad \text{(XIII)-a}$$

wherein $R^5$, $R^9$, n, m and M are as defined above, according to either of the Reaction Schemes C and J.

The amine compound of the formula (XIV) is a known compound.

The reaction of the 1,4-dihydropyridine derivative of the formula (XIII) with the amine compound of the formula (XIV) is carried out in a solvent, in the presence of a basic compound, if required, by application of heat.

Examples of the solvent include such aromatic hydrocarbons as benzene, toluene, xylene and pyridine; and such halogenated hydrocarbons as dichloromethane, chloroform, 1,2-dichloroethane and trichloroethane. Examples of basic compound include such tertiary amines as trimethylamine, triethylamine, tripropylamine, N,N-dimethylaniline and pyridine; and such inorganic basic compound as sodium carbonate, and sodium hydrogen carbonate.

The amine compound of the formula (XIII) may be used in an amount of 0.8 to 5 moles per mole of the 1,4-dihydropyridine derivative of the formula (XIII). The basic compound may be used in an amount of 0.8 to 1.5 moles per mole of the 1,4-dihydropyridine derivative of the formula (XIII).

The reaction temperature is from 25° C. to 180° C., preferably from 50° C. to 120° C. The reaction time varies depending upon the reaction temperature, the amount of reagent and the solvent, etc. Usually, it is about 1 to 24 hours.

The desired compound can be isolated and purified, for instance, by extraction, crystallization, chromatographyc etc.

The obtained product may be subjected to a salt-forming reaction, if required. The salt-forming reaction can be carried out in the same way as discribed above with regard to Reaction SCheme A.

The 1,4-dihydropyridine derivative or its acid addition salt proposed by this invention can thus be produced according to the foregoing Reaction Schemes A–L.

The 1,4-dihydropyridine derivative or its acid addition salt of this invention has a highly potential pharmacological action such as antihypertensive action, vasodilative action, etc. and the remarkably long duration of pharmacological action. Accordingly, the 1,4-dihydropyridine derivative or its pharmaceutically acceptable acid addition salt of this invention is useful as the remedies for the circulatory system diseases including an antihypertensive agent, cerebral vasodilator, cerebral blood flow disturbance improver, anti-stenocardiac remedy, anti-cardiac infarction remedy, antiarrhythmic agent, etc.

Accordingly, the present invention also provides a pharmaceutical composition for preventing or treating the circulatory system diseases which comprises the 1,4-dihydropyridine derivative of the formula (I) or its pharmaceutically acceptable acid addition salt used as an active ingredient and pharmaceutically acceptable carrier. The 1,4-dihydropyridine derivative of this invention is useful for making such pharmaceutical composition not only because of its marked efficacy in curing and preventing hypertension, cerebral blood flow disturbance, stenocardia, etc. but also because of its chemical stability and resulting easiness of being made into various dosage forms. The 1,4-dihydropyridine derivative of this invention can be administered orally and parenterally as well including intravenous, subcutanious, intramuscular, percutaneous, and rectal administrations.

As the dosage forms for oral administration, tablets, pills, granules, powders, suspensions, capsules, etc. may be mentioned.

Tablets can be prepared according to the ordinary compressing method by use of such excipients as lactose, starch, crystalline cellulose, etc., such binders as carboxymethyl cellulose, methyl cellulose, polyvinyl pyrrolidine, etc., and such disintegrators as sodium alginate, sodium bicarbonate, sodium lauryl sulfate, etc.

Pills, powders, and granules can also be formed according to the ordinary methods by use of the same adjuvants as those mentioned above.

Solutions and suspensions can be prepared according to the ordinary methods by use of such glycerol esters as tricaprylin, triacetin, etc. and such alcohols as ethanol, etc. Capsules can be prepared by filling capsules of gelatin and the like with granules, powders or liquid preparations.

As the dosage forms for subcutaneous, intramuscular, and intravenous administration uses, there are injections prepared in the form of an aqueous or non-aqueous solutions. In the preparation of aqueous solutions, an isotonic sodium chloride solution and the like are used. As the 1,4-dihydropyridine dirivative of the present invention is comparatively readily soluble in water, it can be easily made into injections. In the preparation of non-aqueous solutions, propylene glycol, polyethylene glycol, olive oil, ethyl oleate, etc., for instance, are used, and, if required, antiseptics, stabilizers, etc. may additionally be used. Injections can be sterilized by filtration through the bacterial filter or by combined use of disinfectants with other adjuvants.

As the dosage forms for percutaneous administration uses, there are, for instance, ointments and creams. Ointments are prepared according to the ordinary method by use of such fatty oils as castor oil, olive oil, etc. and vaseline and creams are prepared likewise by use of fatty oils and emulsifying agents such as diethylene glycol, sorbitan monofatty acid ester, etc.

For rectal administration use, ordinary suppositories in gelatin soft capsules, etc. are used.

The average dosage of the 1,4-dihydropyridine derivative of this invention per patient varies depending upon the disease, administration routes, age and sex distinction of a patient, condition of a disease, etc.; however, it is usual for an adult patient to be given 1–75 mg/day, preferably 5–20 mg/day.

The present invention is described in detail by the following examples.

REFERENTIAL EXAMPLE 1

Synthesis of 3-(N-benzyl-N-methylamino)-2,2-dimethylpropyl acetoacetate (i) To a solution of N-methyl-N-benzylamine hydrochloride (27.2 g) in 2-propanol (78 ml) were added isobutylaldehyde (12.4 g) and paraformaldehyde (11.4 g). The mixture was refluxed for 6 hours. The solvent was removed under reduced pressure (20 mmHg, about 30° C.) to leave a residue. The residue was dissolved in emthanol (200 ml) and then, to its ice-cooled solution was added sodium borohydride (12 g) in small portions with stirring.

After the removal of an ice-bath, the reaction mixture was stirred for 3 hours at the room temperature.

Methanol was distilled off and to the residue was added 20% aqueous sodium hydroxide solution (40 ml) and was extracted with diethyl ether. The Extracts were washed with a saturated aqueous sodium chloride solution and dried over anhydrous sodium sulfate. The solvent was distilled off to leave an oily residue. Distillation of the residue under reduced pressure provede 26.6 g of 3-(N-benzyl-N-methylamino-2,2-dimethyl-popanol, bp2 mmHg 122°–124° C. in a yield of 75.6%.

Physical properties as follows.

NMR (CDCl$_3$) δppm: 7.2 (s, 5H), 5.65 (s, 1H), 3.48 (s, 2H), 3.38 (s, 2H), 2.42 (s, 2H), 2.18 (s, 3H), 0.93 (s, 6H).

IR (neat) $v_{max}^{cm-1}$: 3400, 2980, 1450, 1360, 1040

MS (m/e): 207 (M+)

Hydrochloride Salt.: m.p. 143–145

(ii) One gram of diketen was added dropwise to a stirred solution of 3-(N-benzyl-N-methylamino)-2,2-dimethyl propanol in 1 ml of benzene at 70° C. Sturing was continued for 1.5 hours at 70° C. after the addition. The solvent was distilled off to leave an oily residue. The residue was chromatographed over silica gel to afford 2.8 g of desired 3-(N-benzyl-N-methylamino)-2,2-dimethylpropyl acetoacetate (oily substance).

The physical properties are as follows.

NMR (CDCl$_3$) δppm: 7.35 (s, 5H), 3.57 (s, 2H), 3.38 (s, 2H), 2.28 (s, 2H), 2.18 (s, 3H), 2.15 (s, 3H), 0.89 (s, 6H), IR (neat) $v_{max}^{cm-1}$: 3000, 1720, 1640, 1450, 1360, 1310, 1250, 1150, 1030

MS (m/e): 291 (M+)

REFERENTIAL EXAMPLE 2

Synthesis of 2-fluoro-5-nitrobenzaldehyde (i) To a solution of 3.0 g of 2-fluoro-5-nitrotoluene in 20 ml of acetic anhydride was added dropwise 5 ml of concentrated sulfuric acid. A solution of chromic anhydride (6.0 g) in acetic anhydride (20 ml) was added dropwise to the mixture with stirring during a period of one hour. The reaction temperature maintained below 10° C. during addition with ice-cooling.

After stirring for another couple of hours, the mixture was poured onto 150 ml of ice-water. The mixture was extracted with dichloromethane. An organic phase was collected and washed succesively with a saturated aqueous sodium chloride solution, a saturated sodium bicarbonate solution, and a saturated aqueous sodium chloride solution and then dried over anhydrous sodium sulfate. Solvent was distilled off to provide 4.23 g of desired 2-fluoro-5-nitrobenzaldehyde diacetyl acetal as a yellowish oil in a yield of 80%.

The physical properties are as follows.

IR (neat) $v_{max}^{cm-1}$: 3990, 1754, 1528, 1488, 1348, 1348, 1190, 1092, 1056, 1046, 996

NMR (CDCl$_3$) δppm: 8.48–8.13 (m, 2H), 7.88 (s, 1H), 7.28 (dd, 1H, J=9 Hz), 2.13 (s, 6H)

(ii) To a solution of 2-fluoro-5-nitrobenzaldehyde diacetal (4.2 g) in an aqueous dioxane (ration; Dioxane/H$_2$O=2.5) (25 ml) was added 1 ml of concentrated sulfuric acid and the mixture was refluxed for 30 minutes.

The solvent was concentrated by distillation under reduced pressure. To the residue was added water and the mixture was extracted with dichloromethane. The extracts were washed successively with a saturated aqueous sodium chloride solution, a saturated aqueous sodium bicarbonate and a saturated aqueous sodium chloride solution.

After dried over anhydrous sodium sulfate, solvent was distilled off to leave an orange colored oil. By a method of column chromatography on silica gel, the desired 2-fluoro-3-nitrobenzaldehyde (1.96 g) was obtained as slightly yellowish needles in a yield of 78%. The physical properties were as follows.

m.p.: 59°–60° C.

IR (KBr) $v_{max}^{cm-1}$: 1690, 1618, 1524, 1348, 1252

NMR (CDCl$_3$) δ: 10.20 (2, 1H), 8.77–8.32 (m, 2H), 7.42 (dd, 1H, J=9 Hz)

REFERENTIAL EXAMPLE 3

Synthesis of 2-fluoro-3-nitrobenzaldehyde

To a solution of 3.0 g of 2-fluoro-3-nitrotoluene in 20 ml of acetic anhydride was added dropwise 4 ml of concentrated sulfuric acid. A solution of chromium trioxide (5.0 g) in 20 ml of acetic anhydride was added dropwise to the mixture with stirring during a period of one hour. The reaction temperature maintained below 10° C. during addition with ice-cooling.

After stirring for another 2 hours, the mixture was poured onto 150 ml of ice-water. The precipitate was separated and washed with 2% aqueous sodium bicarbonate solution to yield solid residue. The residue was dissolved in a mixture of 10 ml of dioxane, 4 ml of water and 0.4 ml of concentrated sulfuric acid, and then refluxed for 30 minutes. The solvent was removed under reduced pressure, and then extracted with dichloromethane. The extracts were washed with a saturated aqueous sodium chloride solution and deied over anhydrous sodium sulfate. The solvent was distilled off to yield 3.0 g of the desired compound.

m.p.: 46°–47° C.

IR (KBr) $v_{max}^{cm-1}$: 1690, 1610

NMR (CDCl$_3$) δppm: 10.54 (s, 1H) 8.56–8.14 (m, 2H), 7.69–7.34 (m, 1H).

Other 2,3-disubstituted benzaldehyde compounds can be obtained likewise.

REFERENTIAL EXAMPLE 4

Synthesis of 2-chloro-3-fluorobenzaldehyde

A solution of 332 μl of anhydrous dimethylsulfoxide (DMSO) in 5 ml of dichloromethane was cooled to −50° C. in an orgon atomosphere. To the solution was added 737 mg of trifluoroacetic acid anhydride with stirring. After the formation of a colorless precipitate, to the mixture was added a solution of 376 mg of 2-chloro-3-fluorobenzylalcohol in dichloromethane, and then stirred at −50° C. for 30 minutes. To the mixture was added a solution of 2.36 g of triethylamine in dichloromethane and then stirred at room temperature for 2 hours.

The reaction mixture was successively washed with a saturated aquous sodium chloride solution, 1N aquous hydroxyde a solution and a saturated aquous sodium chloride solution, and then dried over anhydrous sodium sulfate and concentrated. The residue was purified by column chromatography (eluting solvent; dichloromethane:n-hexane=1:1) to provide 230 mg (Yield 62%) of the desired compound.

NMR (CDCl$_3$) δppm: 7.2–7.8 (m, 2H) 10.5 (1H, s)

IR (KBr) $\nu_{max}^{cm-1}$: 1700, 1600, 1580, 1440, 1305, 1275,
MS (m/e): 160, 158 (M+).

REFERENTIAL EXAMPLE 5

Synthesis of 3-(N-benzyl-N-methylamino)-2,2-dimethylpropyl 3-aminocrotonate

A solution of 5.07 g of 3-(N-benzyl-N-methylamino)-2,2-dimethylpropyl acetoacetate in 15 ml of ethanol was cooled with ice-water. The solution was bubled gasous ammonia and then stirred at room temperature. The solution stood at room temperature overnight. To the solution was added ice-water, and then a precipitated white solid was removed. The solid was washed with water and dried under reduced pressure to yield 4.79 g of the desired compound.

m.p.: 68°–70° C.

IR (KBr) $\nu_{max}^{cm-1}$: 1648, 1624, 1552, 1292, 1164, 1002

NMR (CDCl$_3$) $\delta$ppm: 7.12 (s, 5H), 4.40 (s 1H), 3.80 (s, 2H), 3.45 (s, 2H), 2.26 (s, 2H), 2.10 (s, 3H), 1.76 (s, 3H), 0.86 (s, 6H).

EXAMPLE 1

Synthesis of 2-(N-benzyl-N-methylamino)ethyl methyl 2,6-dimethyl-4-(2,3-dichlorophenyl)-1,4-dihydropyridine-3,5-dicarboxylate (100)

To a solution of 350 mg of 2,3-dichlorobenzaldehyde in 2 ml of 2-prapanol were added 510 mg of 2-(N-benzyl-N-methylamino)ethyl acetoacetate and 250 mg of methyl 3-aminocrotonate. The mixture was refluxed for 12 hours. The solvent was distilled off in vacuo, and then the residue was chromatographed over silica gel with a mixture of chloroform and ethyl acetate as eluting solvents to yield 600 mg of the desired compound. The physical properties are as follows.

IR (CHCl$_3$) $\nu_{max}^{cm-1}$: 1690, 1614

NMR (CDCl$_3$) $\delta$ppm: 7.38–6.98 (m, 8H), 6.01 (brs. 1H), 5.45 (s, 1H), 415 (t, 2H, J=6 Hz), 3.56 (s, 3H), 3.45 (s, 2H), 2.58 (t, 2H, J=6 Hz), 2.23 (s, 6H), 2.13 (s, 3H) ((100) hydrochloride).

A corresponding hydrochloride salt of the compound (100) was prepared by adding an ethereal hydrogen chloride solution to the product (100).

Physical properties are as follows.

IR (KBr) $\nu_{max}^{cm-1}$: 3430, 2620, 1690.

EXAMPLE 2

Synthesis of 2-(N-benzyl-N-methylamino)ethyl methyl 2,6-dimethyl-4-(2-chloro-3-nitrophenyl)-1,4-dihydropyridine-3,5-dicarboxylate (102)

A mixture of 370 mg of 2-chloro-3-nitrobenzaldehyde, 252 mg of methyl 3-aminocrotonate and 506 mg of 2-(N-benzyl-N-methylamino)ethyl acetoacetate in 2 ml of 2-propanol was refluxed for 12 hours and then, the solvent was distilled off in vacuo. The residue was purified by a method of a column chromatography on silica gel with a mixture of chloroform and ethylacetate as eluting solvents. The obtained product (102) (508 mg) has the following physical properties which support its chemical structure.

IR (CHCl$_3$) $\nu_{max}^{cm-1}$: 1692, 1616, 1466,

NMR (CDCl$_3$) $\delta$ppm: 7.73–7.20 (m, 8H), 6.07 (brs. 1H), 5.52 (s, 1H), 4.16 (t, 2H, J=6 Hz), 3.58 (s, 3H), 3.46 (s, 2H), 2.58 (t, 2H, J=6 Hz), 2.28 (s, 6H), 2.14 (s, 3H)

(102 ) hydrochloride.

IR (KBr) $\nu_{max}^{cm-1}$: 3425, 2625, 1692, 1532, 1488.

EXAMPLE 3

Synthesis of 2-(N-benzyl-N-methylamino)ethyl methyl 2,6-dimethyl-4-(2-fluoro-3-nitrophenyl)-1,4-dihydropyridine-3,5-dicarboxylate (104)

A mixture of 330 mg of 2-fluoro-3-nitrobenzaldehyde, 252 mg of methyl 3-aminocrotonate and 506 mg of 2-(N-benzyl-N-methylamino)ethyl acetoacetate in 2 ml of 2-propanol was refluxed for 12 hours, and then the solvent was distilled off in vacuo. The residue was purified by the method of a column chromatography on silica gel to provide 492 mg of the desired compound (104).

IR (CHCl$_3$) $\nu_{max}^{cm-1}$: 1692, 1614, 1462

NMR (CDCl$_3$) $\delta$ppm: 7.94–7.55 (m, 2H), 7.27 (s, 5H), 7.06 (m, 1H), 5.83 (brs, 1H), 5.31 (s, 1H), 4.13 (t, 2H, J=6 Hz), 3.59 (s, 3H), 3.48 (s, 2H), 2.60 (t, 2H, J=6 Hz), 2.30 (s, 6H), 2.15 (s, 3H)

Ms m/e: 497 (M+), 480, 466

(104) hydrochloride

IR (KBr) $\nu_{max}^{cm-1}$: 3425, 2600, 1692, 1530, 1490.

EXAMPLE 4

Synthesis of 2-(N-benzyl-N-methylamino)ethyl methyl 2,6-dimethyl-4-(3-chloro-2-fluorophenyl)-1,4-dihydropyridine-3,5-dicarboxylate (106)

A mixture of 320 mg of 3-chloro-2-fluorobenzaldehyde, 252 mg of methyl 3-aminocrotonate and 510 mg of 2-(N-benzyl-N-methylamino)ethyl acetoacetate in 2 ml of 2-propanol was refluxed for 6 hours, and then the solvent was distilled off in vacuo. The residue was purified by the methods of a column chromatography on silica gel to yield 500 mg of the desired compound (106)

IR (CHCl$_3$) $\nu_{max}^{cm-1}$: 1688, 1616, 1452

NMR (CDCl$_3$) $\delta$ppm: 7.27–6.85 (m, 8H), 5.99 (brs, 1H), 5.24 (s, 1H), 4.13 (t, 2H, J=6 Hz), 3.58 (s, 3H), 3.47 (s, 2H), 2.60 (t, 2H, J=6 Hz), 2.26 (s, 6H), 2.15 (s, 3H)

MS m/e: 486 (M+), 455, 338

(106) hydrochloride m.p.: 109°–112°

IR (KBr) $\nu_{max}^{cm-1}$: 3425, 2600, 1688, 1490.

EXAMPLE 5

Synthesis of 2-(N-benzyl-N-methylamino)ethyl methyl 2,6-dimethyl-4-(3-chloro-2-nitrophenyl)-1,4-dihydropyridine-3,5-dicarboxylate (108)

A mixture of 556 mg of 3-chloro-2-nitrobenzaldehyde, 362 mg of methyl 3-aminocrotonate and 820 mg of 2-(N-benzyl-N-methylamino)ethyl acetoacetate in 4 ml of 2-propanol was refluxed for 6 hours, and then the solvent was distilled off under reduced pressure. The residue was purified by a method of column chromatography onon silica gel to yield 900 mg of the desired compound (108).

IR (CHCl$_3$) $\nu_{max}^{cm-1}$: 1692, 1614, 1465,

NMR (CDCl$_3$) $\delta$ppm: 7.40–7.20 (brs. 8H), 5.85 (brs, 1H), 5.24 (s, 1H), 4.13 (t, 2H, J=6 Hz), 3.58 (s, 3H), 3.47 (s, 2H), 2.62 (t, 2H, J=6 Hz), 2.26 (s, 6H), 2.15 (s, 3H)

MS m/e: 515, 513 (M+)

(108) hydrochloride

IR (KBr) $\nu_{max}^{cm-1}$: 3420, 1692, 1532, 1488.

EXAMPLE 6

Synthesis of 2-(N-benzyl-N-methylamino)ethyl methyl 2,6-dimethyl-4-(2-chloro-3-fluorophenyl)-1,4-dihydropyridine-3,5-dicarboxylate (110)

A mixture of 460 mg of 2-chloro-3-fluorobenzaldehyde, 360 mg of methyl 3-aminocrotonate and 820 mg of 2-(N-benzyl-N-methylamino)ethyl 3-aminocrotonate in 4 ml of 2-propanol was refluxed for 8 hours, and then the solvent was distilled off under reduced pressure. The residue was purified by a column chromatography on silica gel to provide 860 mg of the desired compound (110).

IR (CHCl$_3$) $\nu_{max}{}^{cm-1}$: 1688, 1616, 1452

NMR (CDCl$_3$) $\delta$ppm: 7.27–6.85 (m, 8H), 5.95 (brs, 1H), 5.28 (s, 1H), 4.20 (t, 2H, J=6 Hz), 3.58 (s, 3H), 3.45 (s, 2H), 2.60 (t, 2H, J=6 Hz), 2.26 (s, 6H), 2.15 (s, 3H)

(110) hydrochloride

IR (KBr) $\nu_{mas}{}^{cm-1}$: 3420, 2620, 1692, 1620, 1490.

EXAMPLE 7

Synthesis of 3-(N-benzyl-N-methylamino)-2,2-dimethylpropyl methyl 2,2-dimethyl-4-(3-chloro-2-nitrophenyl)-1,4-dihydropyridine-3,5-dicarboxylate (132)

A mixture of 185 mg of 3-chloro-2-nitrobenzaldehyde, 118 mg of methyl 3-aminocrotonate and 292 mg of 3-(N-benzyl-N-methylamino)-2,2-dimethylpropyl acetoacetate in 1 ml of 2-propanol was refluxed for 12 hours, and then the solvent was distilled off under reduced pressure. The residue was purified by a method of column chromatography on silica gel to yield 337 mg of the desired compound (132).

NMR (CDCl$_3$) $\delta$ppm: 7.4–7.0 (brs, 8H), 6.15 (brs, 1H), 5.28 (s, 1H), 3.92 (s, 2H), 3.60 (s, 3H), 3.41 (s, 2H), 2.21 (s, 8H), 2.04 (s, 2H), 0.80 (s, 6H).

(132) hydrochloride

IR (KBr) $\nu_{max}{}^{cm-1}$: 3400, 1684, 1536, 1480.

EXAMPLE 8

Synthesis of 3-(N-benzyl-N-methylamino)-2,2-dimethylpropyl methyl 2,6-dimethyl-4-(2,3-dichlorophenyl)-1,4-dihydropyridine-3,5-dicarboxylate (134)

A mixture of 175 mg of 2,3-dichlorobenzaldehyde, 126 mg of methyl 3-aminocrotonate and 320 mg of 3-(N-benzyl-N-methylamino)-2,2-dimethylpropyl acetoacetate in 1 ml of 2-propanol was refluxed for 8 hours, and then the solvent was distilled off under reduced pressure. The residue was purified by a column chromatography on silica gel to provide 260 mg of the desired compound (134).

IR (CHCl$_3$) $\nu_{max}{}^{cm-1}$: 1686, 1464, 1116, 1098

NMR (CDCl$_3$) $\delta$ppm: 7.37–7.00 (m, 8H), 5.88 (brs, 1H), 5.47 (s, 1H), 3.91 (s, 2H), 3.58 (s, 3H), 3.44 (s, 2H), 2.23 (s, 8H), 2.05 (s, 3H), 0.84 (s, 6H).

(134) hydrochloride m.p.: 124°–127

IR (KBr) $\nu_{max}{}^{cm-1}$: 3450, 1688, 1492, 1380.

EXAMPLE 9

Synthesis of 3-(N-benzyl-N-methylamino)-2,2-dimethylpropyl methyl 2,6-dimethyl-4-(2-chloro-3-nitrophenyl)-1,4-dihydropyridine-3,5-dicarboxylate (136)

(i) A mixture of 128.7 mg of 2-chloro-3-nitrobenzaldehyde, 88 mg of methyl 3-aminocrotonate and 220 mg of 3-(N-benzyl-N-methylamino)-2,2-dimethylpropyl acetoacetate in 1 ml of 2-propanol was refluxed for 8 hours, and then the solvent was distilled off under reduced pressure. The residue was purified by a column chromatography on silica gel to yield 200 mg of desired compound (136).

NMR (CDCl$_3$) $\delta$ppm: 7.6–7.0 (m, 8H), 5.65 (brs, 1H), 5.50 (s, 1H), 3.95 (s, 2H), 3.66 (s, 3H), 3.46 (s, 2H), 2.30 (s, 8H), 2.08 (s, 3H), 0.89 (s, 6H)

(136) hydrochloride m.p.: 128°–132°

IR (KBr) $\nu_{max}{}^{cm-1}$: 3400, 1686, 1532, 1490, 1428.

(ii) Into a solution of 984 mg of 2-chloro-3-nitrobenzaldehyde and 620 mg of methyl acetoacetate in 10 ml of toluene was bubled gasous hydrogen chloride with ice-cooling for 15 min. The mixture stood overnight with sealing at the room temperature.

To the mixture was added 10 ml of benzene and the resulting mixture was washed with a saturated aqueous sodium chloride solution. The organic layer was dried over anhydrous sodium chloride solution. The solvent was distilled off in vacuo to give quantitatively methyl 2-($\alpha$-chloro-3-nitrobenzyl)acetoacetate (NMR (CDCl$_3$) $\delta$ppm: 7.7–7.1 (m, 3H), 5.9 (d, 1H, J=10 Hz), 4.4 (d, 1H, J=10 Hz), 3.5 (s, 3H), 2.4 (s, 3H)).

To a solution of the compound above-mentioned in 5 ml of isopropanol were added 1.50 g of 3-(N-benzyl-N-methylamino)-2,2-dimethylpropyl 3-aminocrotonate and 530 mg of triethylamine. The mixture was refluxed overnight. The solvent was distilled off in vacuo. The residue was chromatographed on silica gel eluting with a mixture of n-hexane and ethyl acetoacetate (ratio; 2:1) to give 2.09 g of the desired compound (136) with the identical physical properties with those of the compound (136) in the Example 9-(i), same physical property values as those obtained with the compound of the preceding (i).

(iii) 1.50 g of 3-(N-benzyl-N-methylamine)-2,2-dimethylpropyl acetoacetate was added to 2-($\alpha$-chloro-2-chloro-3-nitrobenzyl) methyl acetoacetate which was obtained according to the preceding (ii) and the mixture was dissolved in 5 ml of 2-propanol. Further, 1 ml of concentrated aqueous ammonia was added to the solution and the mixture was heated under reflux for 5 hours. After the reaction was over, the solvent was distilled away. CH$_2$Cl$_2$ was added to the residue, washed with water, and dried over Na$_2$SO$_4$. The solvent was removed by distillation under reduced pressure. The obtained residue was chromatographed on a column of silica gel to obtain 1.5 g of the desired compound (136).

(iv) 335 mg of 1-dibromomethyl-2-chloro-3-nitrobenzene, 115 mg of methyl acetoacetate, and 290 mg of 3-(N-benzyl-N-methylamino)-2,2-dimethylpropyl 3-aminocrotonate were dissolved in 1 ml of 2-propanol. 200 mg of triethylamine was further added thereto and the mixture was heated under reflux. After the solvent was distilled away, the residue was purified by column chromatography on silica gel to obtain 150 mg of the desired compound (136). The physical properties of this compound agreed entirely with those of the compound obtained in the preceding (i).

(v) 340 mg of 1-dibromomethyl-2-chloro-3-nitrobenzene, 290 mg of 3-(N-benzyl-N-methylamino)-2,2-dimethylpropyl acetoacetate, and 120 mg of methyl acetate were dissolved in 1 ml of 2-propanol. 200 mg of triethylamine was further added to the solution and the mixture was refluxed while heating for 10 hours. After the reaction was terminated, the solvent was distilled away. Upon purification of the obtained residue by column chromatography on silica gel, 140 mg of the desired compound (136) was obtained. The obtained compound had the physical properties which coincided with those of the compound obtained in the preceding (i).

EXAMPLE 10

Synthesis of 3-(N-benzyl-N-methylamino)-2,2-dimethylpropyl methyl 2,6-dimethyl-4-(2-fluoro-3-nitrophenyl)-1,4-dihydropyridine-3,5-dicarboxylate (130)

(i) A mixture of 169 mg of 2-fluoro-3-nitro-benzaldehyde, 116 mg of methyl 3-aminocrotanate and 291 mg of 3-(N-benzyl-N-methylamino)-2,2-dimethylpropyl acetoacetate in 1 ml of 2-propanol was refluxed for 8 hours.

The solvent was distilled off under the reduced pressure. The residue was purified by a column chromatography on silica gel to yield 150 mg of the desired compound (130).

IR (CHCl$_3$) $v_{max}^{cm-1}$: 1684, 1464, 1348, 1116

NMR (CDCl$_3$) $\delta$ppm: 7.7–7.5 (m, 2H), 7.3–7.1 (m, 6H), 6.19 (brs, 1H), 5.39 (s, 1H), 3.95 (s, 2H), 3.62 (s, 3H), 3.47 (s, 2H), 2.35 (s, 8H), 2.08 (s, 3H), 0.90 (s, 6H).

Element analysis for C$_{29}$H$_{34}$FN$_3$O$_6$: Calculated (%): C, 64.6: H, 6.4: N, 7.8 Found (%): C, 64.5: H, 6.8: N, 7.6.

(130) hydrochloride m.p.: 170° C.

IR (KBr) $v_{max}^{cm-1}$: 1686, 1536, 1492, 1348, 1206, 1096

Elemental analysis for C$_{29}$H$_{35}$ClFN$_3$O$_6$: Calculated (%): C, 60.5: H, 6.1: N, 7.3 Found (%). C, 60.2: H, 6.4: N, 7.2.

(ii) To a solution of 208 mg of 2-fluoro-3-nitrobenzaldehyde in 1 ml of piperidine. The mixture was stirred with ice-cooling overnight to the reaction mixture was added dichloromethane and the mixture was washed with a saturated aqueous sodium chloride solution and then, the solvent was distilled off to give methyl 2-(2-fluoro-3-nitrovenzylidene)acetoacetate (NMR (CDCl$_3$) $\delta$ppm: 8.0~6.8 (m, 4H), 3.8 (s, 3H), 2.3 (s, 3H)).

To it was added a solution of 350 mg of 3-(N-benzyl-N-methylamino)-2,2-dimethylpropyl 3-aminocrotonate in 1 ml isopropanol. The mixture was refluxed overnight.

The solvent was distilled off in vacuo to leave a residue. The residue was chromatographed over silica gel eluted with a mixture of n-hexane and ethyl acetoacetate (ratio; 2:1) to yield the desired compound (130). The physical properties were identical to those of the compound in the example 10-(i).

(iii) Into a solution of 3.5 g of 2-fluoro-3-nitrobenzaldehyde and 6.0 g of 3-(N-benzyl-N-methylamino)-2,2-dimethylpropyl acetoacetate in 20 ml of toluene was bubled gasous hydrogen chloride with ice-cooling for 15 min. The mixture stood with sealing overnight. An separating aqueous layer was removed and the organic layer was washed with a saturated aqueous sodium chloride solution and then dried over anhydrous sodium sulfate.

The solvent was distilled off in vacuo to leave 3-(N-benzyl-N-methylamino)-2,2-dimethylpropyl 2-($\alpha$-chloro-2-fluoro-3-nitrovenzyl)acetoacetate. The residue was dissolved in 30 ml of sipropanol and to the solution were added methyl 3-aminocrotonate and 2.0 g of triethylamine. The mixture was refluxed for 3 hours. The solvent was distilled off under reduced pressure. The residue was dissolved in methylene chloride and the solution was washed with a solution of saturated aqueous sodium chloride solution and then dried over anhydrous sodium sulfate. After the removal of solvent, the residue was recrystallized from a mixture of ethyl acetate and n-hexane to give 4.0 g of the purified compound (130).

(iv) To solution of 2.3 g of methyl acetoacetate in 30 ml of isopropanol were added 5 ml of concentrated aqueous ammonia and 3-(N-benzyl-N-methylamino)-2,2-dimethylpropyl 2-($\alpha$-chloro-2-fluoro-3-nitrobenzyl) acetoacetate which was obtained according to the same method as the Example 10-(iii).

The mixture was refluxed for 5 hours. The reaction mixture was worked up in the same way as the Example 10-(iii) to provide 2.5 g of the desired compound (130).

(v) To a solution of 1.70 g of 2-fluoro-3-nitrobenzaldehyde in 10 ml of isopropanol were added 1.15 g of methyl 3-aminocrotonate and 2.10 g of 3-chloro-2,2-dimethylpropyl acetoacetate. The mixture was refluxed for 5 hours. Solvent was distilled off under reduced presoure to leave a residue. The residue was chromatographed on silica gel to give 2.09 g of 3-chloro-2,2-dimethylpropyl methyl 2,6-dimethyl-4-(2-fluoro-3-nitrophenyl)-1,4-dihydropyridine-3,5-dicarboxylate.

It was mixed with 5 ml of toluene and to the mixture was added 1.0 g of N-methyl benzylamine. The mixture was refluxed for 8 hours. The mixture was washed with a saturated aqueous sodium chloride solution and then dried over anhydrous sodium sulfate. The solvent was distilled off under reduced pressure to leave a residue. The residue was chromatographed on silica gel to give 1.5 g of the desired compound (130).

EXAMPLE 11

Synthesis of 3-(N-benzyl-N-methylamino)-2,2-dimethylpropyl methyl 2,6-dimethyl-4-(2-fluoro-5-nitrophenyl)-1,4-dihydropyridine-3,5-dicarboxylate (140)

(i) To a solution of a mixture 290 mg of 3-(N-benzyl-N-methylamino)-2,2-diethylpropyl acetoacetate and 15 mg of methyl 3-aminocrotonate in 1 ml of 2-propanol was added 168 mg of 2-fluoro-5-nitrobenzaldehyde. The mixture was refluxed for 10 hours. The solvent was distilled off to leave the residue. The residue was purified by a column chromatography (n-hexane:ethyl acetate=2:1) on silica gel to provide 184 mg (yield 34%) of the desirec compound (140).

IR (CHCl$_3$) $v_{max}^{cm-1}$: 3450, 2950, 1686, 1616, 1466, 1346, 1308, 1118, 1100

NMR (CDCl$_3$) $\delta$ppm: 8.23–7.76 (m, 2H), 7.16 (s, 5H, 6.94 (ad, 1H, J=9 Hz), 6.60 (brs, 1H), 5.28 (s, 1H), 3.84 (s, 2H), 3.56 (s, 3H), 3.39 (s, 2H), 2.30 (s, 3H), 2.26 (s, 5H), 2.05 (s, 3H), 0.86 (s, 6H).

Elemental analysis for C$_{29}$H$_{34}$FN$_3$O$_6$: Calculated (%): C, 64.6: H, 6.4: N, 7.8 Found (%): C, 64.6: H, 6.6: N, 7.4.

(140) hydrochloride

IR (KBr) $v_{max}^{cm-1}$: 3325, 1708, 1656, 1530, 1490, 1346, 1226, 1116

Elemental analysis for C$_{29}$H$_{35}$ClFN$_3$O$_6$: Calculated (%): C, 60.5: H, 6.1: N, 7.3 Found (%): C, 60.2: H, 6.4: N, 7.0.

(ii) To a solution of 350 mg of methyl 3-aminocrotonate in 3 ml of propanol was added 1.40 g of 3-(N-benzyl-N-methylamino)-2,2-dimethylpropyl 2-(2-fluoro-5-nitrobenzylidene)acetoacetate. The mixture was refluxed for 6 hours. The reaction mixture was worked up in the same way as the Example 11-(ii) to give 750 mg of the desired compound (140).

(iii) To a solution of 1.35 g of 3-(N-benzyl-N-methylamino)-2,2-dimethylpropyl 2-(2-fuloro-5-nitrobenzylidene)acetoacetate in 3 ml of 2-propanol were added 350 mg of methyl acetoacetate and 400 μl of concentrated aqueous ammonia. The mixture was refluxed for 6 hours. The reaction mixture was warked up in the same way as the Example 11-(i) to yield the desired compound (140).

EXAMPLE 12

Synthesis of 2-(N-benzyl-N-methylamino)ethyl methyl 2,6-dimethyl-4-(2-fluoro-5-nitrophenyl)-1,4-dihydropyridine-3,5-dicarboxylate (144)

A mixture of 170 mg of 2-fluoro-5-nitrobenzaldehyde, 126 mg of methyl 3-aminocrotonate and 253 mg of 2-(N-benzyl-N-methylamino)ethyl acetoacetate in 1 ml of 2-propanol was reacted and then purified in the same way as in Example 9 to yield 200 mg of the desired compound (144).

IR (CHCl$_3$) $v_{max}^{cm-1}$: 3450, 1692, 1618, 1468, 1348, 1306, 1120, 1104

NMR (CDCl$_3$) δppm: 8.26–7.72 (m, 2H), 7.12 (s, 5H), 6.87 (t, 1H, J=9 Hz), 6.37 (s, 1H), 5.23 (s, 1H), 4.06 (t, 2H, J=6 Hz), 3.53 (s, 3H), 3.40 (s, 2H), 2.55 (t, 2H, J-6 Hz), 2.26 (s, 6H), 2.12 (s, 3H)

(144) hydrochloride

IR (KBr) $v_{max}^{cm-1}$: 3450, 1685, 1520, 1345.

EXAMPLE 13

Synthesis of 3-(N-benzyl-N-methylamino)-2,2-dimethylpropyl methyl 2,6-dimethyl-4-(5-chloro-2-fluorophenyl)-1,4-dihydropyridine-3,5-dicarboxylate (142)

A mixture of 160 mg of 5-fluoro-2-fluorobenzaldehyde, 126 mg of methyl 3-aminocrotonate and 290 mg of 3-(N-benzyl-N-methylamino)-2,2-dimethylpropyl acetoacetate in 2 ml of 2-propanol was reacted and then purified in the same way as in Example 9 to yield 210 mg of the desired compound (142).

IR (CHCl$_3$) $v_{max}^{cm-1}$: 1692, 1468, 1300, 1116, 1102,

NMR (CDCl$_3$) δ: 7.56–6.66 (m, 8H), 6.38 (brs, 1H), 5.25 (s, 1H), 3.90 (s, 2H), 3.62 (s, 3H), 3.44 (s, 2H), 2.26 (s, 6H), 2.21 (s, 2H), 2.05 (s, 3H), 0.85 (s, 3H), 0.84 (s, 3H)

IR (CHCl$_3$) $v_{max}^{cm-1}$: 3450, 1695, 1615, 1465 (142) hydrochloride

IR (KBr) $v_{max}^{cm-1}$: 3450, 1690

EXAMPLE 14

Synthesis of 3-(N-benzyl-N-methylamino)-2,2-dimethylpropy ethyl 2,6-dimethyl-4-(2-fluoro-5-nitrophenyl)-1,4-dihydropyridine-3,5-dicarboxylate (160)

A mixture of 169 mg of 2-fluoro-5-nitrobenzaldehyde, 290 mg of 3-(N-benzyl-N-methylamino)-2,2-dimethylpropyl acetoacetate and 129 mg of ethyl 3-aminocrotanate in 1 ml ml of 2-propanol was reacted and then purified in the same way as in Example 9 to yield 195 mg of the desired compound (160).

IR (CHCl$_3$) $v_{max}^{cm-1}$: 3450, 1590, 1615, 1465, 1350

NMR (CDCl$_3$) δppm: 8.2–7.7 (m, 2H), 7.16 (s, 5H), 6.94 (dd, 1H, J=9 Hz), 6.65 (brs, s. 1H), 5.28 (s, 1H), 4.00 (q, 2H, J=6 Hz), 3.80 (s, 3H), 3.38 (s, 2H), 2.22 (s, 8H), 2.05 (s, 3H), 1.05 (t, 3H, J=6 Hz), 0.80 (s, 6H).

EXAMPLE 15

Synthesis of 3-(N-benzyl-N-methylamino)-2,2-dimethylpropyl methyl 2,6-dimethyl-4-(2-chloro-5-nitrophenyl)-1,4-dihydropyridine-3,5-dicarboxylate (148)

A mixture of 185 mg of 2-chloro-5-nitrobenzaldehyde, 118 mg of methyl 3-aminocrotonate and 292 mg of 3-(N-benzyl-N-methylamino)-2,2-dimethylpropyl acetoacetate in 1 ml ml of 2-propanol was reacted and then purified in the same way as in Example 9 to yield 215 mg of the desired compound (148).

IR (CHCl$_3$) $v_{max}^{cm-1}$: 3450, 1695, 1615, 1360

NMR (CDCl$_3$) δppm: 8.2–7.2 (m, 3H), 7.15 (s, 5H), 6.63 (brd s, 1H), 5.23 (s, 1H), 3.83 (s, 2H), 3.55 (s, 3H), 3.39 (s, 2H), 2.27 (s, 6H), 2.26 (s, 2H), 2.03 (s, 3H), 0.86 (s, 6H)

(148) hydrochloride

IR (KBr) $v_{max}^{cm-1}$: 3450, 1690, 1465.

EXAMPLE 16

Synthesis of 3-(N-benzyl-N-methylamino)-2,2-dimethylpropyl methyl 2,6-dimethyl-4-(2-nitrophenyl)-1,4-dihydropyridine-3,5-dicarboxylate (300)

A mixture of 152 mg of 2-nitrobenzaldehyde, 118 mg of methyl 3-aminocrotonate and 292 mg of 3-(N-benzyl-N-methylamino)-2,2-dimethylpropyl acetoacetate in 1 ml of 2-propanol was reacted and then purified in the same way as in Example 9 to yield 195 mg of the desired compound (300).

IR (CHCl$_3$) $v_{max}^{cm-1}$: 3440, 2940, 1690, 1528, 1466, 1350, 1204, 1112, 1094

NMR (CDCl$_3$) δppm: 7.7–7.2 (m, 9H), 5.87 (brs, 1H), 5.24 (s, 1H), 3.91 (s, 2H), 3.54 (s, 3H), 3.39 (s, 2H), 2.25 (s, 5H), 2.23 (s, 3H), 2.02 (s, 3H), 0.80 (s, 6H)

(300) hydrochloride

IR (KBr) $v_{max}^{cm-1}$: 1690, 1530, 1492, 1356, 1212, 1112, 1092.

EXAMPLE 17

Synthesis of
3-(N-benzyl-N-methylamino)-2,2-dimethylpropyl methyl
2,6-dimethyl-4-(3-nitrophenyl)-1,4-dihydropyridine-3,5-dicarboxylate (302)

A mixture of 152 mg of 3-nitrobenzaldehyde, 118 mg of methyl 3-aminocrotonate and 229 mg of 3-(N-benzyl-N-methylamino)-2,2-dimethylpropyl acetoacetate in 1 ml of 2-propanol was reacted and then purified in the same way as in Example 9 to yield 230 mg of the desired compound (202).

IR (CHCl$_3$) $\nu_{max}{}^{cm-1}$: 3438, 2952, 1692, 1528, 1468, 1351, 1121, 1101.

NMR (CDCl$_3$) δppm: 8.1–7.2 (m, 9H), 6.18 (brs, 1H), 5.13 (s, 1H), 3.90 (s, 1H), 3.62 (s, 3H), 3.40 (s, 2H), 2.38 (s, 3H), 2.26 (s, 3H), 2.18 (s, 2H), 2.02 (s, 3H), 0.83 (s, 3H), 0.80 (s, 3H)

(302) hydrochloride

IR (KBr) $\nu_{max}{}^{cm-1}$: 1684, 1526, 1484, 1344, 1208, 1112, 1088.

EXAMPLE 18

Synthesis of
3-(N-benzyl-N-methylamino)-2,2-dimethylpropyl methyl
2,6-dimethyl-4-(3-chloro-2-fluorophenyl)-1,4-dihydropyridine 3,5-dicarboxylate (156)

(i) To a solution of 15.85 g of 3-chloro-2-fluorobenzaldehyde in 120 ml of toluene was added 11.6 g of methyl acetoacetate. Into the mixture was bubled gasous dry hydrogen chloride at 0°–5° C. for 15 min.

The mixture sealed tightly stood at 0°–5° C. overnight.

To the mixture was added 80 ml of benzene and then, a separated aqueous layer and removed. An organic layer was washed with a saturated aqueous sodium chloride solution and then, dried over anhydrous sodium sulfate. The solvent was distilled off in vacuo to leave an oily residue of methy 2-(α-chloro-3-chloro-2-fluorobenzyl)-acetoacetate. The residue was dissolved in 40 ml of 2-propanol and to the solution was added 30.2 g of 3-(N-benzyl-N-methylamino)-2,2-dimethylpropyl 3-aminocrotonate and 10.1 g of triethylamine. The mixture was refluxed for 3 hours. The solvent was distilled off under reduced pressure. The residue was dissolved in 200 ml of methylene chloride and the washed with water and dried over anhydrous sodium sulfate. After removal of the solvent, the residue was recrystallized from a mixture of ethyl acetate and n-hexane to give 37.0 g of the desired compound (156) (free base) with following physical properties.

NMR (CDCl$_3$) δppm: 7.2–6.8 (m, 8H), 5.90 (brs, 1H), 5.20 (s, 1H), 3.85 (s, 2H), 3.60 (s, 3H), 3.42 (s, 2H), 2.28 (s, 5H), 2.26 (s, 3H), 2.02 (s, 3H), 0.88 (s, 6H), IR (CHCl$_3$) $\nu_{max}{}^{cm-1}$: 3450, 1690, 1650, Elemental analysis for C$_{29}$H$_{34}$ClFN$_2$O$_4$: Calculated (%): C, 65.8: H, 6.5: N, 5.3 Found (%): C, 66.0: H, 6.8: N, 5.2

(ii) (156) Hydrochloride

To a solution of 32.5 g of free base (156) in 200 ml of methylene chloride was added 10 ml of concentrated hydrochloric acid. The mixture was shaked and the organic layer was washed with 30 ml of a saturated aqueous sodium chloride solution and then dried over anhydrous sodium sulfate. After removal of the solvent, the residue was recrystallized from ethyl acetate to give 33.5 g of the desired hydrochloride salt with the following characteristics.

m.p.: 195°–198° C.

IR (KBr) $\nu_{max}{}^{cm-1}$: 3450, 1690, 1495, 1450, 1380,

Elemental analysis for C$_{29}$H$_{35}$Cl$_2$FN$_2$O$_4$: Calculated (%): C, 61.6: H, 6.2: N, 5.0 Found (%): C, 61.5: H, 6.5: N, 4.9

(iii) To a solution of methyl 2-(3-chloro-2-fluorobenzylidene acetoacetate (3,72 g) in 14 ml of 2-propanol was added 4.63 g of 3-(N-benzyl-N-methylamino)-2,2-dimethylpropyl 3-aminocrotonate. The mixture was refluxed for 6 hours. The reaction mixture was worked up in the same manners as the Example 18(i) to give 5.8 g of the desired compound (156) with the identical physical properties as those of the product in the Example 18(i).

(iv) To a solution of 158.5 mg of 3-chloro-2-fluorobenzaldehyde and 116 mg of methylacetoacetate in 1 ml of 2-pranol was added 291 mg of 3-(N-benzyl-N-methylamino)-2,2-dimethylpropyl 3-aminocrotonate. To the mixture was added 0.1 ml of concentrated aqueous ammonia. The resulting maxture was refluxed for 9 hours. The solvent was distilled off under reduced pressure. The residue was chromatographed over silica gel to give the desired compound (156) with the identical physical properties to those of the compound in the Example 18-(i).

(v) To a solution of 372 mg of methyl 2-(3-chloro-2-fluorobenzyldene)-acetoacetate in 1 ml of 2-propanol were added 291 mg of 3-(N-benzyl-N-methylamino)-2,2-dimethylpropyl acetoacetate and 0.1 ml of concentrated aqueous ammonia. The mixture was refluxed overnight. The solvent was distilled off in vacuo to leave a residue. The residue was chromatographed on silica gel to give the desired compound (156) with the identical physical properties to those of the compound in the Example 18-(i).

(iv) To a solution of 158.5 mg of 3-chloro-2-fluorobenzaldehyde were adde 291 mg or 3-(N-benzyl-N-methylamino)-2,2-dimethylpropyl 3-aminocrotonate and 116 mg of methyl acetoacetate. The mixture was refluxed overnight. The solvent was distilled off in vacuo to give a residue. The reaction was treated in the same ways as the Example 18-(iii) to give the desired product (156) which has the identical physical properties with those of the compound of the Example 18-(i).

EXAMPLE 19

Synthesis of
3-(N-benzyl-N-methylamino)-2,2-dimethylpropyl ethyl
2,6-dimethyl-4-(2-fluoro-3-nitrophenyl)-1,4-dihydropyridine-3,5-dicarboxylate (162)

A mixture of 184 mg of 2-fluoro-3-nitrobenzaldehyde, 324 mg of 3-(N-benzyl-N-methylamino)-2,2-dimethylpropyl acetoacetate and 138 mg of ethyl 3-aminocrotonate in 1 ml of 2-propanol was reacted and then purified in the same way as in Example 8 to yield 120 mg of the desired compound (162).

IR (CHCl$_3$) $\nu_{max}{}^{cm-1}$: 1680, 1348, 1096

NMR (CDCl$_3$) δppm: 7.8–6.8 (m, 8H), 6.35 (brs, 1H), 5.27 (s, 1H), 4.00 (q, 2H, J=7 Hz), 3.84 (s, sH), 3.39 (s, 2H), 2.25 (s, 8H), 2.03 (s, 3H), 1.18 (t, 3H, J=7 Hz), 0.85 (s, 6H), (130) hydrochloride IR (KBr) $\nu_{max}{}^{cm-1}$: 1676, 1486, 1204, 1088.

EXAMPLE 20

Synthesis of 3-(N-benzyl-N-methylamino)-2,2-dimethylpropyl isopropyl 2,6-dimethyl-4-(2-fluoro-3-nitrophenyl)-1,4-dihydropyridine-3,5-dicarboxylate (164)

A mixture of 183 mg of 2-fluoro-3-nitrobenaldehyde, 153 mg of 3-(N-benzyl-N-methylamino)-2,2-dimethylpropyl acetoacetate and 153 mg of isopropyl 3-aminocrotonate in 1 ml of 2-propanol was reacted and then purified in the same way as in Example 8 to yield 125 mg of the desired compound (164).

IR (CHCl$_3$) $\nu_{max}^{cm-1}$: 1674, 1348, 1094

NMR (CDCl$_3$) δppm: 7.8–6.8 (m, 8H), 6.05 (brs, 1H), 5.24 (s, 1H), 4.86 (m, 1H), 3.82 (s, 2H), 3.38 (s, 2H), 2.23 (s, 8H0), 2.02 (s, 3H), 1.3–0.9 (m, 6H), 0.84 (s, 3H), 0.83 (s, 3H).

(164) hydrochloride

IR (KBr) $\nu_{max}^{cm-1}$: 1678, 1484, 1348, 1208, 1096.

EXAMPLE 21

Synthesis of 3-(N-benzyl-N-methylamino)-2,2-dimethylpropyl methyl 2,6-dimethyl-4-(2-chloro-6-fluorophenyl)-1,4-dihydropyridine-3,5-dicarboxylate (168)

A mixture of 170 mg of 2-chloro-6-fluorobenzaldehyde, 137 mg of methyl 3-aminocrotonate and 345 mg of 3-(N-benzyl-N-methylamino)-2,2-dimethylpropyl acetoacetate in 2 ml of 2-propanol was reacted and then purified in the same way as in Example 8 to yield 36 mg of the desired compound (168).

NMR (CDCl$_3$) δppm: 7.45–6.8 (m, 8H), 5.82 (brs, 1H), 5.70 (s, 1H), 3.95 (q, 2H, J=15 Hz), 3.61 (s, 3H), 3.48 (s, 2H), 2.25 (s, 5H), 2.18 (s, 3H), 2.08 (s, 3H), 0.87 (s, 6H)

IR (KBr) $\nu_{max}^{cm-1}$: 3350, 1680, 1650, 1610, 1495, 1450, 1210.

(168) hydrochloride

IR (KBr) $\nu_{max}^{cm-1}$: 3450, 1680, 1640, 1615.

REFERENTIAL EXAMPLE 6

3-(N,N-dimethylamino)-2,2-dimethyl methyl 2,6-dimethyl-4-(3-chloro-2-fluorophenyl)-1,4-dihydropyridine-3,5-dicarboxylate (i) To a solution of 1.71 g of 3-(N,N-dimethylamino)-2,2-dimethylpropanol (Reference: M. S. Newman et al; Journal of Medicinal chemistry, vol 15, p1003 (1972)) in 2 ml of benzene was added dropwise 1.16 g of diketene with stirring at 70° C. The mixture was stirred at 70° C. for additional 1.5 hr. Solvent was distilled off in cacuo to leave a yellowish oil. The residue was dissolved in diethyl ether and then extracted with an aqueous 2N-hydrochloric acid solution. The extracts were made alkaline with an aqueous 2N sodium hydroxide solution. The mixture was extracted with diethyl ether and then the ethereal extract was washed with a saturated aqueous sodium chloride solution, and then dried over anhydrous sodium sulfate. The solvent was distilled off to give 2.8 g of 3-(N,N-dimethylamino)-2,2-dimethylpropyl acetoacetate can oily substance. The physical properties of this compound are as follows.

NMR (CDCl$_3$) δppm: 3.95 (s, 2H), 3.47 (s, 2H), 2.25 (s, 9H), 2.13 (s, 2H), 0.85 (s, 6H)

IR (Neat) $\nu_{max}^{cm-1}$: 3000, 1720, 1453, 1362.

(ii) To a solution of 158.5 mg of 3-chloro-2-fluorobenzaldehyde in 2 ml of 2-propanol were added 126.5 mg of methyl 3-aminocrotonate and 236.5 mg of 3-(N,N-dimethylamino)-2,2-dimethylpropyl acetoacetate. The mixture was refluxed for 8 hours. The solvent was distilled off under reduced pressure. The residue was dissolved in diethyl ether and then, extracted with an aqueous 1N hydrochloric acid solution. An aqueous layer was separated and was made alkaline with a 1N aqueous sodium hydroxide solution with ice-cooling. The mixture was extracted with dichloromethane. The extracts were washed with a saturated aqueous sodium chloride solution and dried over anhydrous sodium sulfate. The solvent was distilled off to leave a residue. The residue was chromatographed on aluminum oxide (neutral) eluting with a mixture of ethyl acetate and n-hexane (ratio; 3:2) to yield 80 mg of the desired 3-(N,N-dimethylamino)-2,2-dimethyl methyl 2,6-dimethyl-4-(3-chloro-2-fluorophenyl)-1,4-dihydropyridine-3,5-dicarboxylate. The physical properties of the compound are as follows.

m.p.: 125°–126° C. (from El$_2$O and n-hexane)

NMR (CDCl$_3$) δppm: 7.4–6.8 (m, 3H), 6.32 (brs, 1H), 5.28 (s, 1H), 3.82 (s, 2H), 3,63 (s, 3H), 2.28 (s, 3H), 2.20 (s, 3H), 2.12 (s, 6H), 2.03 (s, 2H), 0.82 (s, 3H), 0.80 (s, 3H).

IR (KBr) $\nu_{max}^{cm-1}$: 3350, 2950, 1705, 1677, 1650, 1615, 1495, 1450, 1205, Hydrochloride IR (KBr) $\nu_{max}^{cm-1}$: 3400, 1695, 1650, 1620, 1495, 1205.

REFERENTIAL EXAMPLE 7

Synthesis of 3-(N,N-dimethylamino)-2,2-dimethylpropyl methyl 2,6-dimethyl-4-(2-chloro-3-nitrophenyl)-1,4-dihydropyridine-3,5-dicarboxylate A mixture of 185.5 mg of 2-chloro-3-nitrobenzaldehyde, 236.5 mg of 3-(N,N-dimethylamino)-2,2-dimethylpropyl acetoacetate and 126.5 mg of methyl 3-aminocrotonate in 2 ml of 2-propanol was reacted and then purified in the same way as in Referetial Example 6, (ii) to yield 100 mg of the desired compound.

m.p.: 167°–169.0° C. (from El$_2$O and n-hexane)

NMR (CDCl$_3$) δppm: 7.80–7.1 (s, 3H), 6.38 (brd, s, 1H), 5.50 (s, 1H), 3.92 (s, 2H), 3.62 (s, 3H), 2.28 (s, 3H), 2.20 (s, 6H), 2.08 (s, 2H), 0.84 (s, 6H), IR (Kbr) $\nu_{max}^{cm-1}$: 3350, 1703, 1655, 1615, 1540, 1495, 1430, 1465, 1305, 1217, Hydrochloride IR (KBr) $\nu_{max}^{cm-1}$: 3450, 1690, 1645, 1610.

EXAMPLE 22

Vasodilative activity in rats periphery

Male SD strain rats, weighing 350 g to 450 g, were used. They were anesthetized with sodium pentobarbital 60 mg/kg i.p.

After heparinized (heparine 1000 μ/kg i.v.), the constant volume blood perfusion was carried out from the left common carotid artery to the lower region of the branching of the renal artery of the abdominal aorta with a constant volume perfusion pump at a rate of 6–7 ml/min. The solution of the test compound was infused into the perfusion blood on the peripheral side with a perfusion pump, and changes in perfusion pressure were measured.

The activity of the test compound was determined as the ratio of the relative activity of the test compound against papaverine obtained from the dose-response curves.

The result of the experiment is shown in Table 1.

TABLE 1

| Compound | Dosage | |
|---|---|---|
| | 0.1 μg/kg | 1 μg/kg |
| (104) hydrochloride | 30 times | 50 times |
| Felodipine | 20 times | 11 times |

EXAMPLE 23

Hypotensive activity by intravenous administration in anesthetized rats

Male Wistar rats weighing about 250 g were used. They were anesthetized with urethane (500 mg/kg) and α-chloralose (100 mg/kg) intraperitoneal injection.

The test compound was dissolved in a small quantity of ethanol and the solution, which was then diluted with physiological saline to have a final concentration of ethanol kept at 5% or lower, was intravenously injected through a catheter inserted into the femoral vein.

The blood pressure was recorded with the pressure transducer via the catheter inserted into the common carotid artery of the rats.

Hypotensive activity of the test compound was indicated by the dose ($ED_{20}$ μ/kg) required for decreasing the mean blood pressure by 20% as compared with the mean blood pressure before the administration.

To determine the duration of the hypotensive action of the test compound, half-life of hypotensive action $T^1/2$ was measured.

These results are as shown in Table 2.

TABLE 2

| Compound | $ED_{20}$ (μg/kg) | Duration $T^1/2$ (min.) (dose) |
|---|---|---|
| (130) hydrochloride | 16.0 | >30 (10) |
| (302) hydrochloride | 9.1 | >30 (10) |
| (156) hydrochloride | 14.9 | 20 (10) |
| Nicardipine hydrochloride | 21.0 | 4.2 (30) |

EXAMPLE 24

Antihypertensive activity by oral administration in conscious rats

Male Wistar rats fasted for then 16 hours weighing about 250 g, had a catheter inserted into the fermoral artery under ether anesthesia and were fixed in the Bollman cage respectively.

When one hour or more passed after the rats were aroused, they were administered the test compound orally. The test compound had been prepared for administration by dissolving in water.

The blood pressure in the femoral artery was recorder and changes in the mean blood pressure were obtained from the following equation. The results are shown in Table 3.

Changes in mean blood pressure (mmHg) =
mean blood pressure (mmHg) after the administration −
mean blood pressure (mmHg) before the administration

TABLE 3

| Compound | Number of animals | Dose mg/kg | Blood Pressure before administration (mmHg) | Changes in mean blood pressure (mmHg) | | | | | | |
|---|---|---|---|---|---|---|---|---|---|---|
| | | | | After 30 min | After 60 min | After 90 min | After 2 hr | After 3 hr | After 5 hr | After 7 hr |
| (140) hydrochloride | 4 | 10 | 112.1 ± 2.5 | −36.7 ± 1.2 | −35.4 ± 2.1 | −36.3 ± 1.8 | −36.2 ± 1.4 | −33.8 ± 1.7 | −32.6 ± 1.4 | −31.7 ± 2.2 |
| (202) hydrochloride | 4 | 10 | 116 ± 2 | −39 ± 4 | −40 ± 4 | −38 ± 5 | −33 ± 5 | −33 ± 3 | −24 ± 4 | −23 ± 5 |
| Nicardipine hydrochloride | 4 | 10 | 116.7 ± 1.8 | −26.7 ± 2.5 | −19.2 ± 2.6 | −18.3 ± 2.8 | −16.3 ± 1.7 | −7.1 ± 1.4 | +1.3 ± 1.9 | +2.5 ± 2.2 |
| Felodipine | 4 | 10 | 123 ± 2 | −34 ± 5 | −27 ± 6 | −24 ± 5 | −22 ± 3 | −17 ± 4 | −10 ± 3 | −5 ± 1 |

EXAMPLE 25

Antihypertensive activity in SHR (Spontaneously Hypertensive Rats)

Male SHR (14 to 16 weeks old) fasted for more than 16 hours were used. Each of the male SHR had a catheter inserted into the femoral artery under either anesthesia and was fixed in the Bollman cage. When one hour or more passed after the rats woke up out of the ether, they were administered the test compound orally. The blood pressure was measured with the pressure transducer via the catheter inserted into the femoral artery.

The test compound was dissolved in a small quantity of ethanol and diluted with water to be adjusted for administration.

Changes in the mean blood pressure were obtained from the equation mentioned below. The Basic and Clinical Study, vol. 14, p. 4495 (1980) is a useful literature to be referred to for making this kind of experiment. The result is shown in Table 4.

Changes in mean blood pressure (mmHg) =
mean blood pressure (mmHg) after the administration −
mean blood pressure (mmHg) before the administration As seen from Table 4, the compound of the present invention shows much stronger antihypertensive action and has a remarkably longer duration of its action than nicardipine.

TABLE 4

| | SHR, under no anesthesia, administered orally | | | | | | | | | |
|---|---|---|---|---|---|---|---|---|---|---|
| Compound | Number of animals | Dose mg/kg | Before administration MBP (mmHg) | Changes in MBP (mmHg) | | | | | | |
| | | | | 30 min. | 60 min. | 90 min. | 2 hr. | 3 hr. | 5 hr. | 7 hr. |
| (106) | 3 | 10 | 177 ± 5 | −56 ± 6 | −53 ± 11 | −46 ± 10 | −47 ± 11 | −39 ± 10 | −37 ± 3 | −31 ± 7 |

TABLE 4-continued

| | | | Before | | | | | | | |
| | Number | | administra- | | | | | | | |
| | of | Dose | tion MBP | Changes in MBP (mmHg) | | | | | | |
| Compound | animals | mg/kg | (mmHg) | 30 min. | 60 min. | 90 min. | 2 hr. | 3 hr. | 5 hr. | 7 hr. |
| --- | --- | --- | --- | --- | --- | --- | --- | --- | --- | --- |
| hydrochloride (130) | 3 | 3 | 171 ± 11 | −67 ± 13 | −62 ± 13 | −60 ± 14 | −54 ± 11 | −48 ± 13 | −40 ± 10 | −29 ± 8 |
| hydrochloride (156) | 4 | 3 | 165 ± 2 | −41 ± 8 | −39 ± 7 | −35 ± 5 | −28 ± 6 | −28 ± 6 | −18 ± 6 | −20 ± 4 |
| hydrochloride (140) | 4 | 3 | 166 ± 9 | −68 ± 2 | −69 ± 4 | −65 ± 2 | −65 ± 2 | −65 ± 2 | −55 ± 2 | −39 ± 5 |
| hydrochloride Nicardipine hydrochloride | 4 | 10 | 171 ± 3 | −28 ± 13 | −29 ± 11 | −17 ± 14 | −18 ± 9 | −12 ± 8 | −10 ± 1 | −11 ± 6 |

SHR, under no anesthesia, administered orally

EXAMPLE 26

Action on mean blood pressure, myocardium, cerebral blood vessels (common carotid artery), and peripheral blood bessels (femoral artery)

A male beagle dog weighing about 10 kg was anesthetized with sodium pentobarbital (35 mg/kg i.v.). The test compound was dissolved in a small quantity of ethanol, diluted with an isotonic sodium chloride solution, and was injected into the right femoral vein.

(i) Action on mean blood pressure

The mean blood pressure (MBP) was measured with the pressure transwer via the cannula inserted into the right femoral artery of the male beagle dog. The changes in the blood pressure after the administration of the test compound are shown in percentages in Table 5.

According to Table 5, the strength of antihypertensive action of nicardipine reaches the peak in one minute after the administration and grows weaker thereafter. On the contrary, the compound of this invention starts increasing its antihypertensive action slowly after the administration and continues performing its antihypertensive action even 15 minutes after the administration. This fact suggests that the compound of this invention has a strong antihypertensive action and the duration of its activity is long.

(ii) Action on myocardium

The left ventricular pressure (LVP) was measured with the pressure transducer via the cannula which was inserted from the left common carotid artery into the left ventricle and the recorded pressure was differentiated to calculate the max (dLVP/db), thus measuring the pharmacological action of the test compound on the myocardium. Table 6 shows the changes in the max (dLVP/dt) in percentages after the administration of the test compound. The Basic and Clinical Study, vol. 14, 4477 (1980) is a useful literature to be consulted with for making this kind of experiment. It is apparent from Table 6 that the compound of this invention has less exciting action on the myocardium than nicardipine.

TABLE 6

| | | Number | Max dLVP/dt | | | | | |
| | Dose | of | Changes in Max dLVP/dt (%) | | | | | |
| Compound | μg/kg i.v. | animals | 0.5 min. | 1 min. | 2 min. | 5 min. | 10 min. | 15 min. |
| --- | --- | --- | --- | --- | --- | --- | --- | --- |
| (140) hydrochloride | 10 | 4 | 0 ± 2 | +2 ± 2 | +2 ± 3 | −6 ± 3 | +6 ± 4 | +4 ± 4 |
| Nicardipine hydrochloride | 10 | 7 | +5 ± 3 | +10 ± 7 | +38 ± 23 | +42 ± 24 | +31 ± 18 | +6 ± 11 |

(iii) Action on cerebral blood vessels (common carotid artery) and action on peripheral blood vessels (femoral artery)

The carotic blood flow (CBF) and the femoral blood flow (FBF) were measured with the electromagnetic blood flowmeter (MFV-1200 made by Japan Photoelectric Co., Ltd.) via probe for measuring the blood flow volume set in the right common carotid artery and the left femoral artery of the male beagle dog respectively.

Table 7 shows the changes in the CBF in percentages after the administration of the test compound.

Table 8 shows the changes in the FBF in percentages after the administration of the test compound.

Table 7 suggests that the increasing CBF reaches the peak one minute after the administration of nicardipine, while the CBF reaches the peak 10-15 minutes after the administration of the compound of this invention and the increase of the flow volume is also remarkably large.

As shown in Table 8, the increasing FBF reaches the peak 2 minutes after the administration of nicardipine, while the FBF reaches the peak 5-10 minutes after the

TABLE 5

| | | Number | Mean Blood Pressure | | | | | |
| | Dose | of | Changes in MBP (%) | | | | | |
| Compound | μg/kg i.v. | animals | 0.5 min. | 1 min. | 2 min. | 5 min. | 10 min. | 15 min. |
| --- | --- | --- | --- | --- | --- | --- | --- | --- |
| (130) hydrochloride | 10 | 4 | −7 ± 1 | −11 ± 1 | −14 ± 1 | −16 ± 2 | −19 ± 3 | −20 ± 3 |
| (140) hydrochloride | 10 | 4 | −6 ± 1 | −10 ± 1 | −15 ± 1 | −20 ± 2 | −23 ± 2 | −28 ± 3 |
| Nicardipine hydrochloride | 10 | 7 | −17 ± 2 | −18 ± 3 | −16 ± 3 | −11 ± 4 | −7 ± 4 | −8 ± 5 | administration of the compound of this invention, from which it can be understood that the compound of this invention has a long duration of peripheral vasodilative action.

TABLE 7

| | | | Carotic Blood Flow (CBF) | | | | |
|---|---|---|---|---|---|---|---|
| | Dose | Number of | Changes in CBF (%) | | | | |
| Compound | μg/kg i.v. | animals | 0.5 min. | 1 min. | 2 min. | 5 min. | 10 min. |
| (140) hydrochloride | 3 | 4 | +7 7 | +14 12 | +17 14 | +22 13 | +22 13 |
| Nicardipine hydrochloride | 3 | 7 | +7 3 | +14 6 | +13 7 | +5 5 | +3 5 |

TABLE 8

| | | | Femoral Blood Flow (FBF) | | | | |
|---|---|---|---|---|---|---|---|
| | Dose | Number of | Changes in FBF (%) | | | | |
| Compound | μg/kg i.v. | animals | 0.5 min. | 1 min. | 2 min. | 5 min. | 10 min. |
| (156) hydrochloride | 3 | 4 | 0 ± 0 | −1 ± 3 | +5 ± 5 | +19 ± 5 | +20 ± 10 |
| Nicardipine hydrochloride | 3 | 7 | +7 ± 7 | +20 ± 9 | +24 ± 0 | +17 ± 10 | +6 ± 0 |

EXAMPLE 27

Hypotensive activity by intravenous administration in anesthetized rat

Male Wistar rats weighing about 300 g were used. The measurement of hypotensive activity was conducted according to the same method as Example 23. The results are as shown in Table 9.

| Compound | $ED_{20}$ (μg/kg) | Duration $T_{\frac{1}{2}}$ (min.) (dose) |
|---|---|---|
| (130)hydrochloride | 14.7 | 15 (10) |
| (156)hydrochloride | 24.5 | 8.5 (30) |
| Comparison | 80.7 | 4.6 (100) |
| | 288.4 | 3.5 (300) |

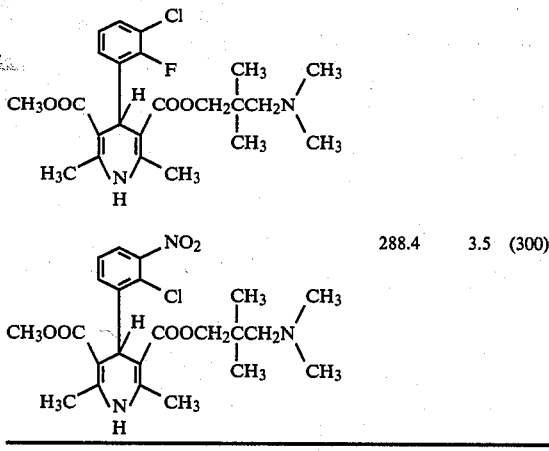

The compounds of the present invention have much stronger antihypotensive activity and longer duration than the compounds of comparison having N,N-dialkylamino alkylester group at the 5-position.

EXAMPLE 28

Activity of calcium ion blocking action

Spillay cut strips of thoracic arota were obtained from male wister rat and mounted in K-depalarized solution. 30–40 min. after treatment of compound (140) hydrochloride various concentration of $Ca^{++}$ were applied and concentration-response curve of calcium ion ($Ca^{++}$) was obtained.

50% inhibited concentration of compound (140) hydrochloride to $Ca^{++}$ contraction was $10^{-10}$M.

50% inhibited concentration of nicardipine hydrochloride to $Ca^{++}$ contraction was twice as much as that of compound (140) hydrochloride.

EXAMPLE 29

In vitro inhibitory activity of platelet aggregation

The in vitro platelet aggregation inhibiting activities of the compounds of the invention were examined by using guinea pigs. Blood was withdrawn by cardiac puncture from male Hartley guinea pigs weighing 4.5 to 5 kg. A mixture of a 3.8% trisodium citrate solution and the blood in a ratio of 1:9 was centrifuged at a speed of 800 rpm for 10 minutes. The upper layer was separated as platelet-rich plasma (PRP). The lower layer was further centrifuged at a separated as platelet-poor plasma (PPP). The number of platelets was adjusted to $5 \times 10^5/\mu l$ to $6 \times 10^5/\mu l$ by filuting the PRP with PPP. 25 microliters of the test compounds prepared as shown below was added in an amount of 25 microliters of PRP after the adjustment, and the mixture was pre-incubated at 37° C. for 2 minutes, and then 75 μM (final) of AA was added. By using an aggregometer (37° C., 1,100 rpm), changes in transmission were recorded.

The test compound was dissolved in ethanol to a concentration of 10 mg/ml. When its activity was measured, it was used after being diluted with phosphate buffer (pH 7.4). Furthermore, after dilution with the buffer, the test compound was left to stand at 0° C. for 4 hours, and the activity of the test compound was similarly measured.

The rate of inhibition of platelet aggregation was determined from the following equation.

$$\text{Inhibition rate (\%)} = \left(1 - \frac{T}{T_c}\right) \times 100$$

The results are shown in Table 10.

TABLE 10

| Compound | Conc. (μM) | Inhibition % AA 75 μM |
|---|---|---|
| (140) hydrochloride | 100 | −1.1 ± 1.4 |
| (156) hydrochloride | 100 | −1.9 ± 2.5 |

TABLE 10-continued

| Compound | Conc. (μM) | Inhibition % AA 75 μM |
|---|---|---|
| Nicardipine hydrochloride | 100 | 35.2 ± 9.4* |

*$P < 0.05$
significantly different from control

It is seen from Table 10 that the compounds of this invention have no inhibitory activity of platelet aggregation, on the contrary nicardipine hydrochloride has inhibitory activity of platelet aggregation. The above fact demonstrates that the compounds of this invention have more specific pharmacological activity than nicardipine hydrochloride.

EXAMPLE 30

Measurement of chemical stability 1 mg of compound (156) hydrochloride was dissolved in 100 ml of methanol. The solution was placed in a transparent glass test tube, and after the test tube was tightly stoppered, it was allowed to stand by the window of the laboratory. Part of the solution was taken at regular intervals and subjected to high performance liquid chromatograph to determined the remaining quantity of compound (156) hydrochloride contained in the solution. The same experiment was conducted with nicardipine hydrochloride as the control.

The result of the experiment is shown in Table 11, from which it is clear that compount (156) hydrochloride has the better light stability than nicardipine hydrochloride.

TABLE 11

Light stability in methanol solution

| Compound | Remaining percentage | | |
|---|---|---|---|
| | 2 hr. | 4 hr. | 6 hr. |
| (156) hydrochloride | 100 | 99 | 100 |
| Nicardipine hydrochloride | 98 | 87 | 78 |

EXAMPLE 31

Preparation of tablets

A tablet containing in one tablet 3 mg of compound (140) hydrochloride is prepared from the following prescription
compound (140) hydrochloride—3 mg
lactose—87 mg
starch—30 mg
magnesium stearate—2 mg

EXAMPLE 32

Preparation of an injectable solution

An aqueous solution for injection containing in 1 ml 0.05 mg of compound (140) hydrochloride is prepared from the following prescription.
compound (140) hydrochloride—5 mg
sodium chloride—900 mg
water for injection—100 ml

EXAMPLE 33

Preparation of powder

A powder having the following components is prepared.
compound (140) hydrochloride—5 mg
lactose—100 mg
starch—100 mg
hydroxypropyl cellulose—10 mg

EXAMPLE 34

Synthesis of 3-(N-benzyl-N-methylamino)-2,2-dimethylpropyl methyl 2-propyl-6-methyl-1,4-dihydropyridine-3,5-dicarboxylate (242)

To a mixture of 330 mg of 2-fluoro-3-nitrobenzaldehyde, 580 mg of 3-(N-benzyl-N-methylamino)-2,3-dimethylpropyl 3-aminocrotonate in 2 ml of 2-propanol was added 260 mg of methyl butyrylacetate. The mixture was refluxed for 12 hr. The resulting reaction mixture was treated in the same way as in Example 8 to give 300 mg of the desired compound (242).

Elemental analysis for $C_{31}H_{38}FN_3O_6$: Calculated (%): C, 65.6: H, 6.7: N, 7.4 Found (%): C, 65.5: N, 6.8: N, 7.2.

EXAMPLE 35

Synthesis of 3-(N-benzyl-N-methylamino)-2,2-dimethylpropyl methyl 6-ethyl-2-methyl-1,4-dihydropyridine-3,5-dicarboxylate (170)

To a solution of 165 mg of 2-fluoro-5-nitrobenzaldehyde, 305 mg of 3-(N-benzyl-N-methylamino)-2,2-dimethylpropyl propioacetate in 1 ml of isopropanol was added 123 mg of methyl 3-aminocrotonate. The mixture was refluxed for 12 hr. The resulting reaction mixture was treated in the same way as in Example 8 to give 125 mg of the desired compound (170).

Elemental analysis for $C_{30}H_{36}FN_3O_6$: Calculated (%): C, 65.1: H, 6.6: N. 7.6 Found (%): C, 65.1: H, 6.4: N. 7.5

What we claim is:
1. A 1,4-dihydropyridine derivative represented by the formula (1)

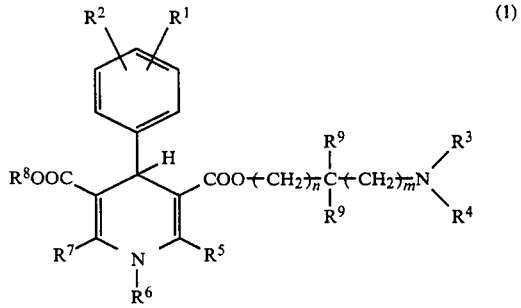

wherein
$R^1$ and $R^2$ are identical or different and each represents a hydrogen atom, a halogen atom or a nitro group, provided that $R^1$ and $R^2$ are not hydrogen atoms at the same time; $R^3$ represents an alkyl group; $R^4$ represents a benzyl or phenethyl group which may be substituted by a substituent selected from the group consisting of a halogen atom, a $C_1$-$C_6$ allyl group, a $C_1$-$C_6$ alkoxy group, and a halogenated methyl group; $R^5$ and $R^7$ are identical or different and each represents an alkyl group; $R^6$ represents a hydrogen atom or an alkyl group; $R^8$ represents an alkyl group; $R^9$ represents a hydrogen atom or an alkyl group; n and m are identical or different and each represents an integer of 0 to 6; provided that when either one of $R^1$ and $R^2$ is a hydrogen atom, $R^9$ is an alkyl group;
or an acid addition salt thereof.

2. The 1,4-dihydropyridine derivative or the acid addition salt thereof according to claim 1 wherein $R^1$ and $R^2$ represent a halogen atom or a nitro group.

3. The 1,4-dihydropyridine derivative or the acid addition salt thereof according to claim 2 wherein $R^1$ and $R^2$ are substituted at the 2- and 3-positions of the phenyl group or substituted at the 2- and 5-positions of the phenyl group.

4. The 1,4-dihydropyridine derivative or the acid addition salt thereof according to claim 1 wherein $R^1$ and $R^2$ represent a halogen atom or a nitro group, and $R^9$ represents an alkyl group.

5. The 1,4-dihydropyridine derivative or the acid addition salt thereof according to any one of claims 1 to 4 wherein n and m represent an integer of 1 to 3.

6. The 1,4-dihydropyridine derivative or the acid addition salt thereof according to any one of claims 1 to 4 wherein $R^6$ represents a hydrogen atom.

7. The 1,4-dihydropyridine derivative or the acid addition salt thereof according to any one of claims 1 to 4 wherein $R^5$ and $R^7$ represent a methyl group.

8. A pharmaceutical for preventing or treating hypertension composition or angina pectoris comprising a pharmaceutically effective amount of the 1,4-dihydropyridine derivative of claim 1 or its pharmaceutically acceptable acid addition salt as an active ingredient and a pharmaceutically acceptable carrier.

9. A medicament in the form of a unit dosage comprising the pharmaceutical composition of claim 8.

10. A method for preventing or treating hypertension or angina pectoris of a warm-blooded animal, which comprises administering a pharmaceutically effective amount of the 1,4-dihydropyridine derivative of claim 1 or its pharmaceutically acceptable acid addition salt.

11. The method of claim 10, wherein the pharmaceutically effective amount is 1 mg–75 mg/day/patient.

* * * * *

UNITED STATES PATENT AND TRADEMARK OFFICE
CERTIFICATE OF CORRECTION

PATENT NO. : 4,578,395

DATED : 3/25/86

INVENTOR(S) : Hisao Yamaguchi et al

It is certified that error appears in the above-identified patent and that said Letters Patent is hereby corrected as shown below:

IN THE CLAIMS:

Claim 1, line 12 (column 48, line 64) change "allyl" to --alkyl--.

Signed and Sealed this

Nineteenth Day of April, 1988

Attest:

DONALD J. QUIGG

Attesting Officer      Commissioner of Patents and Trademarks